United States Patent
Miles et al.

(10) Patent No.: US 10,825,548 B2
(45) Date of Patent: Nov. 3, 2020

(54) SYSTEMS AND METHODS OF SENSING AND ANALYZING ANTIBODY BLOCKING INTERACTIONS

(71) Applicants: Wasatch Microfluidics, Inc., Salt Lake City, UT (US); Rinat Neuroscience Corp., South San Francisco, CA (US)

(72) Inventors: Adam Miles, Salt Lake City, UT (US); Joshua W. Eckman, Salt Lake City, UT (US); Yasmina Abdiche, South San Francisco, CA (US)

(73) Assignees: Carterra, Inc., Salt Lake City, UT (US); Rinat Neuroscience Corp., San Francisco, CA (US)

( * ) Notice: Subject to any disclaimer, the term of this patent is extended or adjusted under 35 U.S.C. 154(b) by 0 days.

(21) Appl. No.: 14/558,109

(22) Filed: Dec. 2, 2014

(65) Prior Publication Data
US 2015/0269312 A1   Sep. 24, 2015

Related U.S. Application Data
(60) Provisional application No. 61/910,795, filed on Dec. 2, 2013.

(51) Int. Cl.
| | |
|---|---|
| G16B 20/00 | (2019.01) |
| G01N 33/68 | (2006.01) |
| G01N 21/552 | (2014.01) |
| G01N 33/577 | (2006.01) |
| G16B 45/00 | (2019.01) |

(52) U.S. Cl.
CPC .......... G16B 20/00 (2019.02); G01N 21/553 (2013.01); G01N 33/577 (2013.01); G01N 33/6854 (2013.01); G16B 45/00 (2019.02)

(58) Field of Classification Search
CPC ...... G16B 20/00; G16B 45/00; G01N 21/553; G01N 33/577; G01N 33/6854
See application file for complete search history.

(56) References Cited

U.S. PATENT DOCUMENTS

| | | | | |
|---|---|---|---|---|
| 8,206,936 B2 * | 6/2012 | Walker | ............. | G01N 33/54306 435/7.1 |
| 2003/0014420 A1 * | 1/2003 | Jessee | ................. | G06F 17/3061 |

FOREIGN PATENT DOCUMENTS

| | | | |
|---|---|---|---|
| WO | WO201258220 A2 | * | 5/2012 |
| WO | WO2012072814 A1 | * | 6/2012 |

OTHER PUBLICATIONS

Abdiche et al., Exploring blocking assays using Octet, ProteOn, and Biacore biosensors, Analytical Biochemistry 386 (2009) 172-180.*

Abdiche et al, "Expanding the ProteOn XPR36 Biosensor into a 36-Ligand Array Expedites Protein Interaction Analysis", Anal. Biochem, Apr. 2011, pp. 139-151, vol. 411, No. 1.

Abdiche et al, "Label-Free Epitope Binning Assays of Monoclonal Antibodies Enable the Identification of Antigen Heterogeneity", J. Immunol. Methods, Aug. 2012, pp. 101-116, vol. 382, No. 1-2.

Abdiche, "Array-Based Label-Free Epitope Binning and Epitope Mapping of Monoclonal Antibodies", Presentation, Jun. 20, 2013, Wasatch Microfluidics Epitope Binning Meeting, San Francisco, CA.

Eddings et al, "Improved continuous-flow print head for microarray deposition", Anal Biochem, 2008, pp. 55-59, vol. 382.

El-Manzalawy et al, "Recent advances in B-cell epitope prediction methods", Immunome Research, 2010, pp. S2, vol. 6, Suppl 2.

Emde et al, "Combining epitope-distinct antibodies to HER2: cooperative inhibitory effects on invasive growth", Oncogene, 2011, pp. 1631-1642, vol. 30.

Estep et al, "High Throughput Solution-Based Measurement of Antibody-Antigen Affinity and Epitope Binning", MAbs, Apr. 2013, pp. 270-278, vol. 5, No. 2.

Jamnani et al, "Targeting high affinity and epitope-distinct Oligoclonal nanobodies to HER2 over-expressing tumor cells", Experimental Cell Research, 2012, pp. 1112-1124, vol. 318.

Klein et al, "Epitope interactions of monoclonal antibodies targeting CD20 and their relationship to functional properties", MAbs, 2013, pp. 22-33, vol. 5.

Koefoed et al, "Rational identification of an optimal antibody mixture for targeting the epidermal growth factor receptor", MAbs, 2011, pp. 584-595, vol. 3.

Markovitz et al, "The diversity of the Immune response to the A2 domain of human factor VIII", Blood, 2013, pp. 2785-2795, vol. 121.

Pishchany et al, "Specificity for human hemoglobin enhances *Staphylococcus aureus* infection", Cell Host Microbe, 2010, pp. 544-550, vol. 8.

Rich et al, "Higher-throughput, label-free, real-time molecular interaction analysis", Anal Biochem, 2007, pp. 1-6, vol. 361.

Robak et al, "Rozrolimupab, a mixture of 25 recombinant human monoclonal RhD antibodies, in the treatment of primary immune thrombocytopenia", Blood, 2012, pp. 3670-3676, vol. 120.

Spangler et al, "Triepitopic Antibody Fusions Inhibit Cetuximab-Resistant BRAF and KRAS Mutant Tumors via EGFR Signal Repression", J Mol Biol, 2012, pp. 532-544, vol. 422.

Sun et al, "Preparation of ultrapure bovine and human hemoglobin by anion exchange chromatography", J Chromat, 2008, pp. 1-7, vol. B 867.

(Continued)

*Primary Examiner* — Andrea S Grossman
(74) *Attorney, Agent, or Firm* — Thorpe North & Western, LLP

(57) ABSTRACT

A system and method for sensing and analyzing antibody blocking interactions is described. A biosensor can be used to identify interactions between antibodies to generate interaction profiles for the antibodies. A processor can be used to assign the antibodies to one or more bins, with the antibodies sharing a common interaction profile assigned to a common bin, and each antibody only being assigned to one bin. The antibodies can be represented by displaying nodes grouped together for antibodies in a common bin. Connections between the nodes can be displayed, representing interactions between the antibodies.

36 Claims, 21 Drawing Sheets

(56) References Cited

OTHER PUBLICATIONS

Torres et al, "*Staphylococcus aureus* IsdB is a hemoglobin receptor required for heme iron utilization", J Bacteriol, 2006, pp. 8421-8429, vol. 188.

\* cited by examiner

= Green  = Red  = Yellow

SYSTEMS AND METHODS OF SENSING AND ANALYZING ANTIBODY BLOCKING INTERACTIONS

BACKGROUND

One step in the engineering of bio therapeutics can include characterizing and grouping a library of monoclonal antibodies by the epitope binding regions generated against a specific antigen. Advances in antibody engineering have allowed for the rapid generation of large libraries of antibodies with therapeutic potential. Researchers searching for new therapeutic antibodies typically first identify leads from a large number, possibly thousands, of potential therapeutic antibodies. Characterizing such a large number of antibodies presents challenges of cost and time to researchers.

Epitope binning is one method that has been used to help identify lead antibodies. An epitope is a part of an antigen that is recognized by the immune system. A single antigen can have multiple epitopes, and specific antibodies can have specificity and affinity for binding to a particular epitope. In epitope binning, antibodies are tested in a pairwise combinatorial manner, and antibodies that compete for the same binding region are grouped together into bins. However, as alluded to, binning with state of the art technology can be a very time consuming process, and thus, improvement in this area may include providing a more efficient system of testing and grouping antibodies.

BRIEF DESCRIPTION OF THE DRAWINGS

Reference will now be made to the exemplary embodiments illustrated, and specific language will be used herein to describe the same. It will nevertheless be understood that no limitation of the scope of the invention is thereby intended by virtue of a provided example.

DETAILED DESCRIPTION

Figure 1:
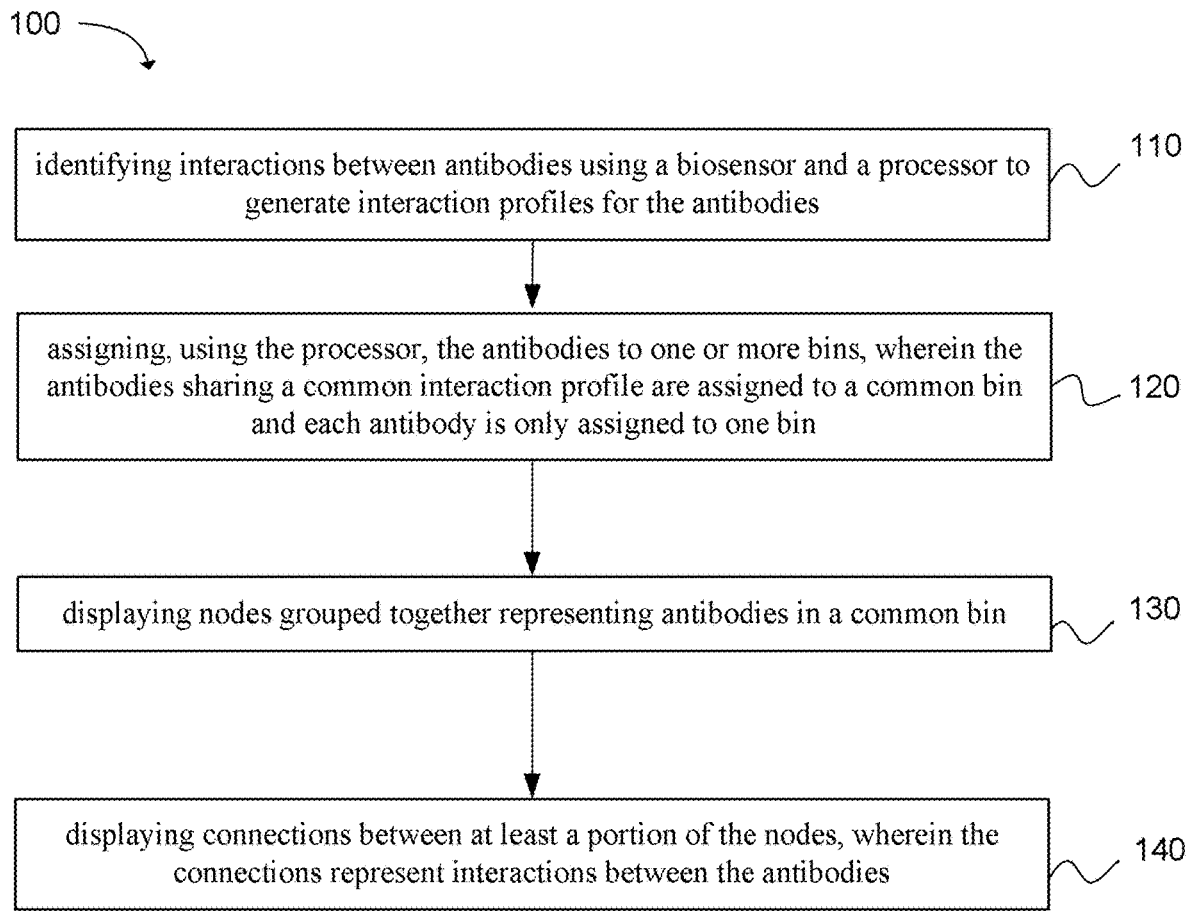
FIG. 1 is a flowchart illustrating an example method of sensing and analyzing antibody blocking interactions.

In accordance with the present disclosure, there can be a benefit in testing and binning a large number of antibodies in order to identify diverse groups of lead antibodies for certain epitope binding profiles for an antigen. However, as also mentioned, binning with state of the art technology can be a very time consuming process. With the present technology, tools are presented for discovering and characterizing the epitopes of a target protein at an early stage, thus, facilitating understanding of function and mechanism of action. This, in turn, allows for a more guided development for therapeutic antibodies. Antibodies that target similar epitopes often share a similar function. Conversely, antibodies that target different epitopes may imply different mechanisms of action. The ability to generate this information early in the drug discovery process enables researchers to reduce the number of potential candidates while maintaining epitope diversity. In accordance with the present disclosure, in epitope binning analysis, each antibody in a test panel is tested against every other antibody in the test panel. Therefore, a test panel of 10 antibodies may benefit from testing 100 interactions, and a test panel of 100 antibodies may benefit from testing all 10,000 interactions. If this can be done quickly, and characterized quickly in an effective manner, powerful information can be understood that can greatly improve the process. For example, testing the interactions in accordance with the present technology can result in a large amount of data that is readily accessible, which can be very helpful for identifying lead antibody candidates for further development.

In the quest for therapeutic monoclonal antibodies (mAbs), the selection of appropriate affinity, specificity, and biophysical properties is highly beneficial. Methodologies that allow an effective candidate to be selected from a large number of leads can make the difference between a successful program and a clinical failure, even when the target has been properly chosen. A mAb's epitope correlates with its functional activity, but the in silico prediction of B-cell epitopes may not yet be possible, so epitope selection remains an empirical process. Early-stage drug discovery efforts often generate large panels of mAbs per target via complementary approaches such as traditional hybridoma and modern phage-display methods, so it is helpful to organize mAbs into epitope families or "bins." For example, MAbs that target similar epitopes often share a similar function, so identifying an epitope bin with functional activity provides several potential leads to choose from. Conversely, if mAbs from multiple epitope bins exhibit functional activity, this may imply different mechanisms of action, which can be advantageous when pursuing an oligoclonal therapy to treat some cancers or infectious diseases where simultaneous targeting of more than one biological pathway may be beneficial.

With the high cost of developing a therapeutic mAb, the ability to identify a few high quality leads with relevant epitopes early in the discovery process would be an advantage over many state of the art methods. To illustrate, while determining the crystal structure of an antigen/mAb complex is the recognized "gold standard" method for defining an epitope with precision at the molecular level, this technique exhibits low-throughput, is labor-intensive, and uses large amounts of highly pure reagents. Therefore, it is not amenable to early-stage research where efforts focus on selecting leads for further characterization. Epitope binning assays on label-free biosensors are an attractive approach for discriminating mAbs in a test panel based upon their binding to a specific antigen because they can be performed at relatively low cost and high throughput without the need for specialized reagents (e.g., only the mAbs and the antigen of interest might be selected for use). Various multiplexed array-based platforms are currently available from the leading vendors of commercial biosensors (e.g., Biacore from GE Healthcare, ProteOn from BioRad, and Octet from FortéBio, a division of Pall Life Sciences), and until recently, they have been able to process 36 or fewer interactions simultaneously and the number and diversity of analyte/ligand interaction pairs that could be explored per unattended assay was limited by various factors including the autosampler capacity and the assay configurations that are amenable on each specific platform.

With the above in mind, an example method of sensing and analyzing antibody blocking interactions is illustrated in FIG. 1. The method 100 may include identifying interactions between antibodies using a biosensor and a processor to generate interaction profiles for the antibodies 110; and assigning, using the processor, the antibodies to one or more bins, wherein the antibodies sharing a common interaction profile are assigned to a common bin and each antibody is only assigned to one bin 120. Additional steps can include displaying nodes grouped together representing antibodies in a common bin 130; and displaying connections between at least a portion of the nodes, wherein the connections represent interactions between the antibodies 140.

The antibodies can be monoclonal antibody samples. Monoclonal antibodies are typically made by identical cloned immune cells. A monoclonal antibody can bind specifically to a single epitope of an antigen. Large libraries of monoclonal antibodies can be quickly developed for a single antigen. For example, a mouse can be injected with a target antigen, and these immune cells can be harvested from the mouse. The immune cells can produce a large number of different antibodies, and individual cells can be cloned and often fused with cancer cells to create a line of cells that produces a single monoclonal antibody. Other techniques can likewise be used, as would be appreciated by one skilled in the art. After creating a library of monoclonal antibodies to investigate, the large of number of antibodies can be narrowed down to a smaller number of lead antibodies through epitope binning.

In epitope binning, antibodies can be tested in a pairwise combinatorial manner, and antibodies that compete for the same binding region can be grouped together into bins. Epitope binning experiments are generally performed using three different protocols: tandem, premix, and classical sandwich blocking. In a classical sandwich assay, one antibody is immobilized onto the surface of a sensor, then the antigen is flowed over the capture antibody. The secondary antibody is then flowed over the antibody/protein complex. In a premix binning assay, an antibody is immobilized on the surface and a premixed solution of the second antibody and antigen is flowed over the antibody. In tandem, the target protein is immobilized on the surface and the two antibodies compete to bind. In each of these techniques, antibodies that block one another can be identified. By testing whether antibodies block one another in a pairwise fashion, an interaction profile can be created for each antibody relative to the others in the library. The interaction profile is the blocking behavior of the antibody with respect to all other antibodies in the library. The blocking profile for a particular antibody includes a list of every other antibody that is blocked by that antibody. Thus, if two antibodies have the same list of other antibodies that they block, those two antibodies exhibit the same blocking behavior and therefore have the same interaction profile. Antibodies that share a common interaction profile can be grouped into a common bin. Since the number of interactions for a comprehensive epitope binning analysis scales geometrically with the number of antibodies in the test panel (i.e., binning ten antibodies is typically based on 100 interactions; and binning 100 antibodies is typically based on 10,000 interactions, though this is not strictly required), an epitope binning assay rapidly escalates into a large experiment. High-throughput epitope binning assays on large panels of antibodies can yield high-resolution binning information because the discriminating power of the assay increases with the epitope diversity within the test panel.

Figure 2A:
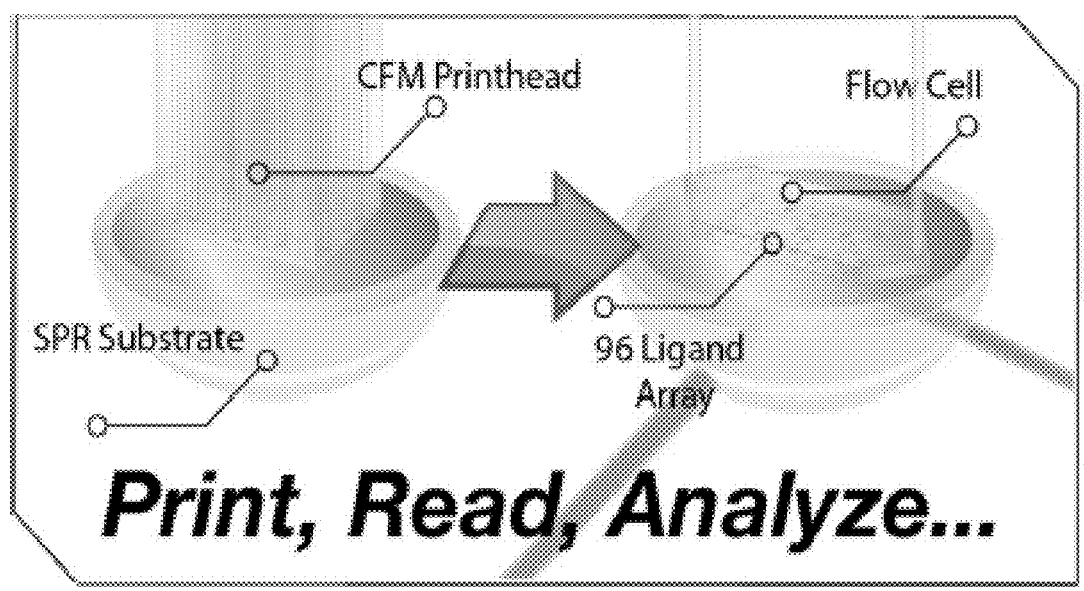
FIG. 2A illustrates an example of a continuous flow microspotting biosensor.
Figure 2B:
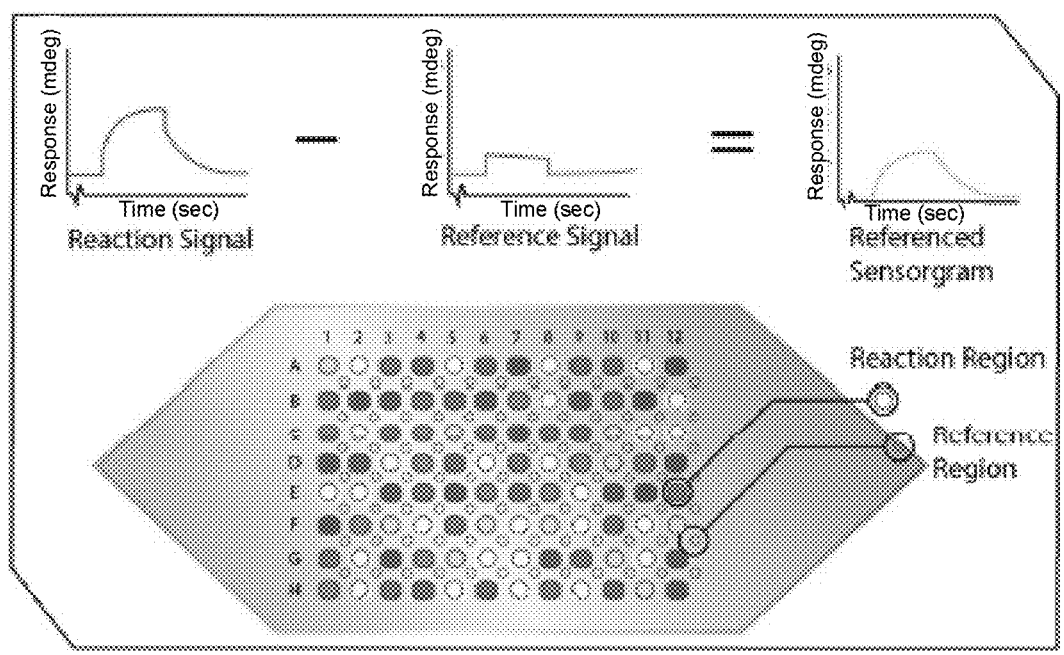
FIG. 2B illustrates an example of an array of spots printed by a continuous flow microspotting printer used for surface plasmon resonance imaging.

In the past, epitope binning has taken significant time, sample volume, and manpower for experimental setup and data analysis. This has limited its application to small numbers of samples. Thus, for practical reasons, binning often occurred later in the development process after the samples were narrowed down to some degree. However, in accordance with the present disclosure, biosensors coupled with analysis tools of the present disclosure have been developed to allow automated testing of larger numbers of antibodies. At least two biosensors have been developed that can be coupled with the computing and analysis tools described herein that enable the simultaneous analysis of 96 analyte/ligand interactions. The first platform uses continuous flow microspotting (CFM) technology to immobilize 96 ligands on a sensor chip, which is then read via surface plasmon resonance imaging (SPRi) within a single flow cell of the IBIS-MX96 instrument. Analytes are accommodated in a 96-well microplate and microfluidics are used to inject them one after another over the 96-ligand array, thereby performing an interaction analysis on 9216 unique analyte/ligand pairs per experiment. FIG. 2A shows a continuous flow microspotting print head and a sensor chip as used in the IBIS-MX96 instrument. FIG. 2B shows the sensor chip ready to be read using SPRi. A second platform is the Octet-HTX, which is a higher-throughput version of the well-established biolayer interferometry (BLI)-based Octet-Red384 platform that has become an industry standard among label-free biosensors. In the BLI system, 96 ligand-coated fiber optic sensor tips dip into a 96-analyte array thereby addressing 96 independent analyte/ligand interactions in parallel. Since the BLI system does not employ microfluidic sample handling, all samples including analytes and common reagents (antigen, buffer and regeneration solutions) are accommodated within two 384-well microplates.

A biosensor and a processor can be used to identify interactions between antibodies, and then generate interaction profiles for the antibodies. The processor can be part of a computer or network of computers. In some embodiments, the processor can be integrated into or with the biosensor, while in other embodiments the processor can be in a separate device. In one embodiment, the processor can be part of a computing device in communication with the biosensor. The computing device can have a graphical user interface for a user to control the computing device and biosensor. For example, the graphical user interface can be used to setup experiments, run experiments, and view displays of experiment results. The processor can run an interaction module. The interaction module can assign interaction profiles to the antibodies. For example, the interaction module can be in communication with a data store where a list of antibodies and a list of interactions are stored. The interaction module can start with one antibody in the list of antibodies and check all interactions that the antibody has with other antibodies. The set of interactions between that antibody and the other antibodies is that antibody's interaction profile. The interaction module can iterate through the list of antibodies and assign an interaction profile to each one.

In one embodiment, the biosensor can be directly connected to a computing device such as a personal computer. This can be in a laboratory or research facility where researchers use the computing device and biosensor to perform experiments. However, other arrangements of computing devices are possible which may include a network of computing devices, a server(s), cloud computing, etc. In some cases, the biosensor can be connected to the Internet and send interaction data to a remote server, where the data is analyzed. The interaction module and other modules performing analysis can be implemented by software installed on a local computing device, a server, or on multiple computing devices. In some cases the software can be a web application usable by researchers on any number of devices.

After interaction profiles are assigned for each antibody, the antibodies can be assigned to bins. A bin can include antibodies that share a common interaction profile. In one example, this may mean that antibodies are in a single bin will have the same blocking behavior, i.e., each antibody blocks the same antibodies as the others in the bin. Additionally, in one example, antibodies within a bin can block other antibodies in the same bin or antibodies in different bins. A bin can also often contain a single antibody. This may occur when an antibody has a unique interaction profile that is not shared by any other antibody in the library of tested antibodies. Thus, an antibody may be assigned to only one bin, because the antibody has only one interaction profile.

Assigning the antibodies to bins can be done using a processor. The processor can be the same processor used to generate interaction profiles, or a different processor. In the context of a method, when referring to "a" processor, and then subsequently referring to "the" processor, this does not infer that the same processor is used for each step, but rather, that one or more processor is used for one step, and one or more processor (same or different) is used for another step. Thus, the term "processor" should be interpreted as referring to a single processor or multiple processors used in any manner or combination to effect the act of processing. In accordance with this processing, a binning module can be run on the processor to assign the antibodies to bins. The binning module can be in communication with a data store where a list of interaction profiles and a list of antibodies are stored. The binning module can create a bin for each distinct interaction profile and assign all antibodies with a particular common interaction profile to the bin for that particular interaction profile. The binning module can store a list of the bins in the data store. Automated binning performed using a processor in this manner can dramatically reduce the man hours to perform an epitope binning analysis.

Data from the binning experiment can be displayed to a user in any manner that is readable by the user. For example, heat maps have been used to display epitope binning data, in which a grid of colored squares represents the interactions between the antibodies. Examples of this type of heat map are shown in FIGS. 3A-D, 4A-C, 5A, 6A-B, 7A, 8A-B, and 9A. In these heat maps, red squares represent a blocking interaction between two antibodies, and green squares represent that they can simultaneously bind to the antigen in different locations. Yellow squares can be used to represent ambiguous interactions. Other colors or shading can be used to represent "one-direction" interactions, in which blocking occurs when one antibody is attached to the antigen first, but no blocking occurs when the other antibody is attached first. Though these colors are used in the examples presented herein, color is not important with respect to displaying the relevant information. This information could and may often be easily replaced with other colors, or other graphical information that is readable to the user. For example, if present in black and white drawings, the various colored squares might be represented by solid black or white, various forms of cross-hatching, or shading, e.g. the green squares could be replaced with white or empty squares (indicating no interaction), the red squares could be replaced by multi-directional cross hatching (indicating blocking interactions), and the yellow squares replaced by one-directional cross hatching (indicating ambiguous interaction or "one-direction" interaction). See FIG. 7B for an example of what black and white cross hatching squares or shapes might look like. These or other designs, patterns, colors, shading, etc., could likewise be used for these or other relevant interactions. For example, in some heat maps, other colors may be used, such as grey, e.g., representing orphan mAbs which were inactive in one orientation but exhibited binding in the other orientations. There may be occasion to use more colors or graphical representations to present additional data, as would be appreciated by one skilled in the art after considering the present disclosure.

Node plots can also be used to display data from epitope binning experiments. Node plots can display more information than a heat map plot in a way that is easy for a viewer to understand. In some embodiments, nodes can be displayed grouped together representing antibodies in a common bin. In other words, nodes can be grouped together for antibodies that have the same blocking behavior in both the ligand direction and the analyte direction. For example, the nodes can be grouped by proximity between the nodes, such as clustering the nodes for a single bin close together. In one embodiment, nodes in a single bin can be represented by displaying an envelope, or outline, surrounding the nodes. Nodes can also be grouped by formatting the nodes themselves, such as by matching node color, shape, border, and so on.

Thus, a viewer can immediately determine upon viewing the node plot, which antibodies belong to which bin. In some embodiments the nodes can also be grouped by other similarities in antibody behavior, besides common bins. Any suitable sorting algorithm can be used to group the nodes together. The node plot can also include connections between the nodes, representing interactions between the antibodies. In some embodiments, the connections can be represented by lines, or chords, connecting nodes.

Examples of node plots are shown in FIGS. 3E, 4D, 5B, 6C, 7C, 8C, and 9B. Referring the FIG. 4D as an example, it can be seen that several bins are represented by grouping nodes in the same bin into colored envelopes surrounding the nodes. In this example, connections are displayed as lines connecting two nodes. Each line on the plot represents a blocking interaction between the antibodies that are connected by the line. Antibodies normally self-block. These self-blocking interactions can be displayed on the plot using the node itself, e.g. a solid linetype for the node border can denote a self-block while a dotted or dashed border could denote a failed self-block. An exemplary bin shown in the figure includes antibodies 88 and 41. These antibodies share a bin because they have the same interaction profile. Specifically, antibody 88 blocks antibody 88 (itself), antibody 41, and antibody 17. Antibody 41 also blocks antibody 88, antibody 41 (itself) and antibody 17. Antibody 17 in this particular experiment is an orphan. Orphan analytes—antibodies that were inactive as ligand or as analyte, but active in the other direction (i.e., 5, 17, 33, 39, 58, 60, 62, 82, and 94, as shown by the grey rows in FIG. 4C)—introduce gaps into the heat map because they were neither tested for self-blocking nor cross-blocking against one another. While tentative bins can be assigned to the orphan analytes based on their blocking against the active ligands, further experiments can be used to determine whether the missing orphan/orphan cross-blocking information would alter those assignments. Thus, each orphan can be inscribed by its own envelope. Orphans 58 and 94 were assigned to the same bin because they exhibited the same blocking profile, i.e., they were not blocked by any ligand, but there is no chord between them because their ability to block one another was not determined. Thus, the plot shows 32 antibodies in 21 epitope bins. In this particular plot, the nodes for anti-IsdB (iron-regulated surface determinant protein B) antibodies are color-coded according to each antibody's functional activity, as determined by their ability to block (red), or not block (green), rIsdB's (recombinant *Staphylococcus aureus* iron-regulated surface determinant protein B) binding to Hb (hemoglobin), which is the natural ligand for native IsdB. As mentioned, black and white shading, cross-hatching, solid black and/or white blocks, etc., could likewise be used without departing from the principles of the present disclosure.

Additional information about the antibodies in the panel, and their cross-blocking relationships, can be depicted via formatting of the nodes and connections. For example, the shape, size, border(s), background color, border color and border line type of the node can be used to report information about the individual antibody and its performance in the cross-blocking assay, such as an antibody which was inactive on the surface but active in solution, or inactive in both directions. In some embodiments nodes can be displayed differently depending on whether the antibody is an orphan or non-orphan. In one case, orphans can be represented by squares while non-orphans are represented by circles. Other graphical information could alternatively be used.

The format of connections, such as line thickness, line type, color, and so on can be used to convey additional information about the interaction between individual antibody pairs, such as the number of replicates for that pair that were present in the assay, heterogeneity in the blocking results (blocking when A is on the surface and B is in solution, but not the reverse), and so on. As shown in the figures, blocking interactions can be displayed by solid lines. In some embodiments, blocking interactions between antibodies in the same bin can be distinguished from blocking interactions between antibodies in different bins. For example, red lines or lines of another color can be used to show inter-bin blocking while black lines can show intra-bin blocking. One-direction blocking can also be displayed differently, such as by a dotted line. In short, color variation and/or line variation (thickness, hash pattern, etc. can be used as may be desired.

Other types of information can also be conveyed by the node plot. In some embodiments, the node plot can display information from results of other assays. The node characteristics can be used to convey information about the antibodies that is determined from other assays, such as the functional activity of the antibodies in a cell-based assay. For example, this information can be represented by changing the background color or pattern of the nodes. Information about kinetic rate constants can also be displayed. For example, on-rate, off-rate, or affinity can be represented by changing the background color or pattern of nodes to colors selected from a color gradient representing a range of values. Additional information can also be conveyed by the node plot by placement of the nodes on a coordinate system that depicts additional information about each of the antibodies. For example, the nodes can be placed on an "isoaffinity plot" with the on-rate as one axis and the off-rate as the other axis. The connections between the nodes can be toggled on and off to visualize how rate constants relate to cross-blocking behavior.

In some embodiments, the node plot can be displayed on an electronic display such as a computer monitor, tablet, smartphone screen, projector, etc. The node plot can be integrated into a graphical user interface of a software program for running experiments with the biosensor and analyzing the data. In some embodiments, the node plot can be displayed by printing onto paper or other media. For example, the software program can include an option to print node plots from a printer attached to the computing device running the software.

In some embodiments, the node plot can be interactive, allowing a user to modify the display of the node plot in real time. For example, in some embodiments the user can highlight individual antibodies or groups of antibodies, as well as the connections between them, such that the rest of the network is hidden or shown in a "grayed-out" color or configuration.

In some embodiments, the graphical user interface can allow a user to combine results of two or more experiments, or test panels, onto a single node plot. To the extent that the same antibodies were present in both panels, new connections can be added to connect additional blocking relationships that those antibodies have with the other antibodies in both panels. The combined node plot can be a union of the nodes and connections of the two test panels (the combined plot can include the nodes for antibodies present in both panels, plus the nodes for antibodies present in only one panel or the other, with connections for all interactions that were found during the experiments). When experiments are combined in this way, some pairwise interactions between antibodies are not tested because some antibodies were not present in both test panels (e.g., if experiment one tested antibodies 1-10 and experiment two tested antibodies 6-15, then antibodies 1-5 and 11-15 would not have been tested against one another). The graphical user interface can allow the user to view the pairwise antibody interactions that were not tested. This could be done with a chord line type, color, etc., connecting those antibodies that were not tested in a pairwise fashion, with the ability to toggle this information off and on.

In another embodiment, a non-transitory computer readable storage medium can contain instructions that can be read by at least one processor in connection with a biosensor to perform the method of sensing and analyzing antibody blocking interactions as described above. Specifically, the instructions can cause the at least one processor and biosensor to identify interactions between antibodies to generate interaction profiles for the antibodies, assign the antibodies to one or more bins, wherein the antibodies sharing a common interaction profile are assigned to a common bin and each antibody is only assigned to one bin, display nodes grouped together representing antibodies in a common bin, and display connections between at least a portion of the nodes, wherein the connections represent interactions between the antibodies.

Figure 10:
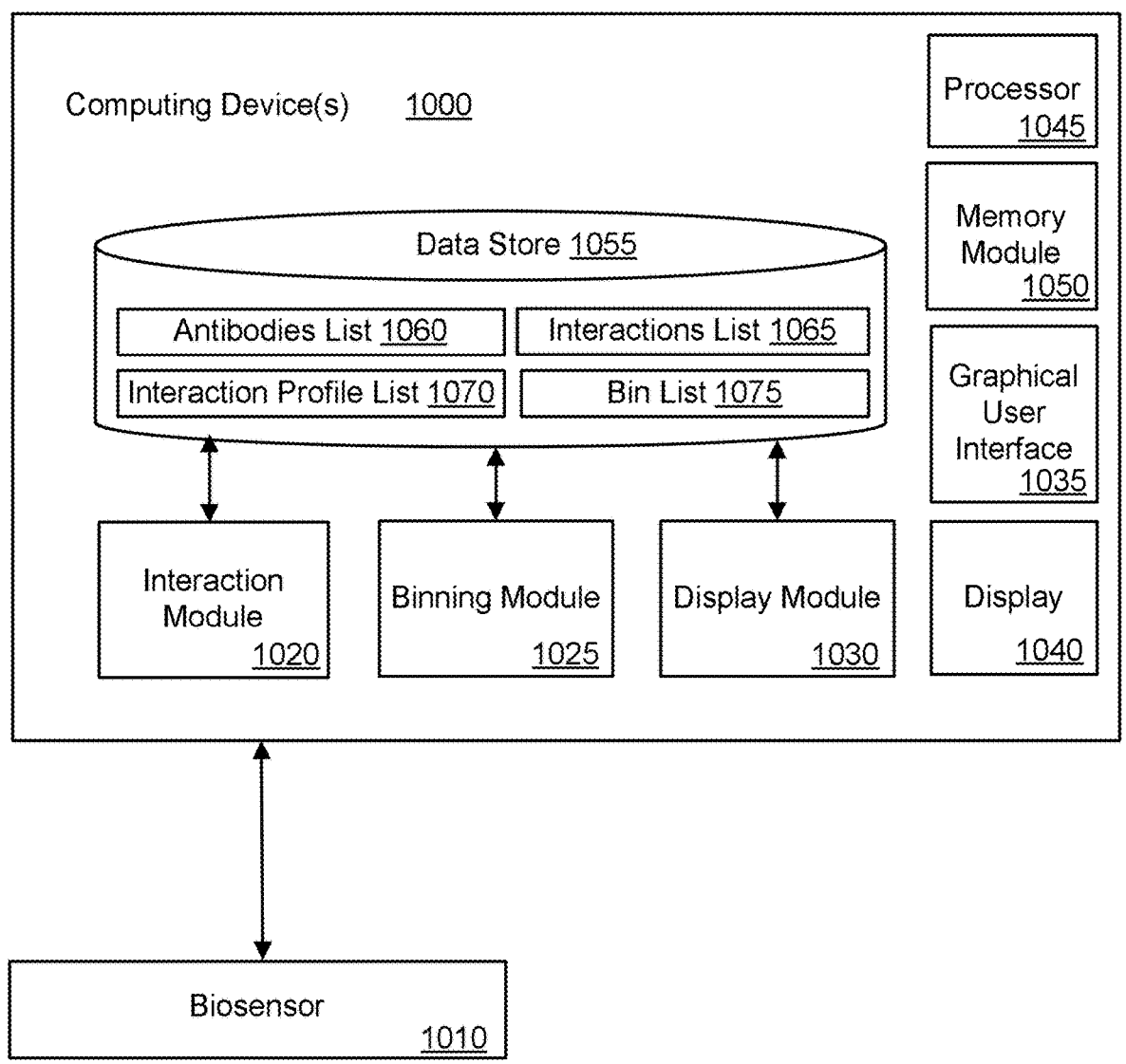
FIG. 10 is a block diagram illustrating an example of a system for sensing and analyzing antibody blocking interactions.

In another embodiment, a system for sensing and analyzing antibody blocking interactions can include a biosensor configured to sense interactions between antibodies. FIG. 10 shows a block diagram of a system including a computing device 1000 and a biosensor 1010. An interaction module 1020 can be configured to receive information about the interactions from the biosensor and identify interaction profiles for the antibodies. A binning module 1025 can be configured to assign the antibodies to one or more bins. Each antibody sharing a common interaction profile can be assigned to a common bin and each antibody can be assigned to only one bin. A display module 1030 can be configured to generate a graphical representation of the bins and interactions. The graphical representation can include nodes grouped together representing antibodies in a common bin, and connections between at least a portion of the nodes, where the connections represent interactions between the nodes. The graphical representation can be displayed as part of a graphical user interface 1035 which is shown on a display 1040. The interaction, binning, and display modules can be run by a processor 1045 and a memory module 1050. Also, the modules can have access to a data store 1055 which can contain an antibodies list 1060, an interactions list 1065, an interaction profile list 1070, and a bin list 1075. The data in the data store can be stored and retrieved by the modules. For example, the interaction module can retrieve information about antibodies and interactions between antibodies from the antibodies list and the interactions list. Then interaction module can also store interaction profiles that have been assigned to antibodies in the interaction profile list. The binning module can retrieve information from the antibodies list and the interaction profile list to assign antibodies to bins, and then store the bins in the bin list. The display module can retrieve information from the antibodies list, the interactions list, the interaction profile list, and the bin list to generate the graphical representation of the bins and interactions.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

Furthermore, both systems and methods are described herein. Any discussions or descriptions related to the system is relevant and fully supports discussions and descriptions of the method, and vice versa, regardless of the context.

Though the following examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended thereby that the disclosure be limited by any specific example.

EXAMPLES

General Reagents

Purified recombinant human progranulin (rhPGRN, catalog number 2420-PG) and biotinylated anti-His mAb (catalog number BAM050) were obtained from R&D Systems (Minneapolis, Minn.). Purified recombinant *Staphylococcus aureus* iron-regulated surface determinant protein B (rIsdB) with a C-terminal 8-His-tag and an N-terminal Flag-tag and Avi-tag and a predicted molecular mass of approximately 68 kDa was prepared in-house. Anti-hPGRN and anti-IsdB mAbs were also generated and purified in-house. Hemoglobin (Hb) was purified in-house from fresh red blood cells obtained from Bioreclamation LLC (Westbury, N.Y.). Briefly, Hb from cell lysates was purified using Q-sepharose XL resin (GE healthcare), followed by Superdex 200 Prep Grade resin (GE healthcare) for size exclusion [14]. Anti-Flag mAb (catalog number F3165) and Flag peptide (catalog number F3290) were purchased from Sigma Inc., St Louis, Mo. Anti-Flag mAb was biotinylated in-house using a five-fold molar excess of EZ link NHS-LC-LC-biotin (catalog number 21343, Pierce Biotechnology, Rockford, Ill.). IgG elution buffer pH 2.8 and amine-coupling activation reagents were also purchased from Pierce. Activation reagents were stored at −20° C. as single-use aqueous aliquots at stock concentrations of 0.4 M 1-ethyl-3-[3-dimethylaminopropyl]-carbodiimide hydrochloride (EDC) and 0.1 M N-hydroxysulfosuccinimide (sulfo-NHS). Amine-coupling buffers (100 mM MES pH 4.5 or pH 5.0) were prepared using 2-(N-Morpholino)ethanesulfonic acid sodium salt (MES, catalog number M3058, Sigma). Amine-coupling blocking reagent (1 M ethanolamine.HCl pH 8.5) was purchased from GE Healthcare. All experiments were conducted at 25° C. in PBS buffer supplemented with 0.01% Tween-20 (SPRi experiments) or 0.05% Tween-20+1 g/l BSA (BLI experiments). Coupled mAbs were regenerated using 75 mM phosphoric acid, unless stated otherwise.

BLI Assays

Octet platforms (HTX, Red384, and QK384) equipped with amine-reactive, streptavidin, and anti-species sensors were purchased from Pall-ForteBio Inc. (Menlo Park, Calif.). Epitope binning experiments were performed in 96-channel mode (HTX system) or 16-channel mode (Red384 and QK384 systems). MAbs were coupled onto amine-reactive sensors on-line using a standard protocol in MES coupling buffer (either pH 4.5 or pH 5.0, depending upon the experiment). Briefly, sensors were soaked in coupling buffer (30 min), activated in a freshly prepared mixture of EDC and sulfo-NHS each diluted 1/10 (from their stock concentrations) in MES buffer, coupled with 30 μg/ml mAb, and excess reactive esters were blocked with ethanolamine. Activation, coupling, and blocking steps were allowed 15 min each. To perform a classical sandwich epitope binning assay, each binding cycle consisted of four steps: 1) a baseline was established in running buffer for 3 min, 2) antigen (5 nM rhPGRN or 10 nM rIsdB) was captured for 10-15 min, 3) mAb analyte (5 μg/ml) was bound for 5-15 min, and 4) the surfaces were regenerated for 30-45 sec. The timing of the binding steps varied, depending upon the experiment. For the anti-IsdB mAbs, the regeneration solutions were optimized per mAb from the following panel (15 mM, 30 mM or 75 mM phosphoric acid; or 6 mM NaOH+ 1M NaCl).

Performing a premix epitope binning assay on sensors coupled with anti-hPGRN mAbs involved a three-step binding cycle; 1) a baseline was established for 3 min, 2) mixtures of 10 nM rhPGRN with or without 200 nM binding sites of each anti-hPGRN mAb were bound for 15 min, and 3) surfaces were regenerated for 30 sec.

To generate surfaces for in tandem epitope binning assay on rIsdB, streptavidin sensors were coated with 2 ug/ml biotinylated capture reagent (anti-His mAb or anti-Flag mAb) for 30 min. The in tandem style assay comprised a five-step binding cycle; 1) a buffer baseline was established for 3 min, 2) 5 μg/ml rIsdB was captured for 5-15 min, 2) 20 μg/ml mAb array was loaded to saturate the immobilized antigen for 5-15 min, 4) 10-20 μg/ml of the test mAb was bound for 5-15 min, and 5) the capture surfaces were regenerated for 30 sec. Anti-His surfaces were regenerated with 75 mM phosphoric acid and anti-Flag surfaces were regenerated using 2:1 v/v Pierce IgG elution buffer/4 M NaCl supplemented with 0.1 g/l Flag peptide. In tandem assays were conducted on all three Octet systems (HTX, Red384, and QK384), depending on the experiment.

The anti-IsdB mAbs were tested for their ability to block the rIsdb/Hb interaction as follows. MAbs were captured at 15 μg/ml via anti-species sensors (10 min), 32 nM rIsdB was bound (10 min) followed by 1 μM Hb. Anti-species sensors were regenerated with 75 mM phosphoric acid. An isotype-matched negative control mAb (not specific for the target antigen) was used to assess any non-specific cross-reaction of rIsdB or Hb.

SPRi and CFM Method

A CFM 2 (Wasatch Microfluidics) was used to create a microarray of 96 mAbs. It draws forty-eight 70-μl plugs of sample from a 96-well microplate into a fluidic manifold which focuses the solutions into a 4×12 array of 48 micro flow cells on the surface of the SPR substrate (a G-COOH coated prism from Ssens bv, NL) and cycles the solutions back and forth at 60 μl/min. A 96-well microplate was prepared with 100 μl of each mAb at 30 μg/ml in 100 mM MES pH 4.5, and loaded into bay 2 of the CFM. A second plate of freshly mixed activating reagents (150 μl aliquot of 0.1 M sulfo-NHS+150 μl 0.4 M EDC diluted 1/60 into 5 ml of 100 mM MES pH 4.5) was loaded into bay 1. The CFM was then primed with system buffer (PBS+0.01% T20). The anti-hPGRN mAb plate contained six replicate sets of sixteen mAbs, and the anti-IsdB mAb plates contained either 32 mAbs arrayed in triplicate or 24 mAbs arrayed in quadruplicate. Once docked, the activating reagents were cycled over the surface for 7 min and followed immediately by the first set of 48 mAbs (top half of the mAb plate) and cycled for 15 min. Without undocking, the spots were rinsed with the system buffer. Because the CFM prints 48 solutions at a time, it will typically address the surface twice to create the full 8×12 array of 96 mAbs. After the first print, the CFM was paused to load fresh activation reagents, and the same cycle of 7-min activation and 15-min coupling was repeated for the second half of the mAb plate.

The printed prism was then loaded into the SPRi reader (MX96, IBIS Technologies bv), which uses a single flow cell and auto-sampler configured to address the array with back-and-forth cycled injections of 80 µl per analyte. Once loaded, 1 M ethanolamine was injected across the chip for 15 min to quench the excess reactive esters. The chip was then washed with system buffer and the chip image was used to define the reaction spots (the mAb array) and the interstitial reference spots (two local reference spots were used to reference each reaction spot). For the premix style binning assay, a standard injection cycle of analyte and regeneration was used. For classical binning, a co-inject was used, where both antigen and mAb analyte were transported to the flow cell in parallel lines, and injected immediately after one another before continuing with regeneration. For classical binning experiments, antigen (16 nM rhPGRN or 35 nM rIsdB) was injected for 3 min, followed by 20 µg/ml mAb for a further 3 min, and then the surfaces were regenerated. For the rhPGRN premix binning experiment, samples were prepared by mixing 8 nM rhPGRN with each mAb in a 10-20 fold molar excess, before injecting each mixture for 10 min followed by a regeneration step. Each SPRi experiment was conducted in a 96×96 analyte-on-ligand format.

Biosensor Data Analysis

Octet data were processed in ForteBio's data acquisition software v. 8.0.0.99 by aligning to zero on the Y-axis prior to the binding step of interest and analyzed by visual inspection to create a heat map. In the heat maps, ligands are listed vertically and analytes are listed horizontally, in the same order. A cell represents an analyte/ligand pair and is color-coded by its blocking status where red—blocked, green—not blocked, and yellow—intermediate or ambiguous response. Self-blocks are outlined with a bold box. A conflicting blocking result for a given mAb pair (i.e., blocks in only one direction of the heat map) is indicated with a dotted border around those cells. Grey rows represent inactive ligands and grey columns indicate the excluded analytes (e.g., due to insufficient sample or poor quality data). SPRi data were processed in SPRint software v. 6.15.2.1 (calibrated, locally referenced, and aligned to zero on the Y-axis prior to the binding step of interest) and analyzed in Wasatch Microfluidics' binning software for heat map generation, sorting and node plotting. In interpreting a node plot, it is assumed that all mAbs in the panel have been tested for pairwise competition against one another so that a chord connects two mAbs that showed a blocking relationship, and no chord represents a non-blocking relationship. MAbs that belong to the same bin are inscribed by the envelopes. The node plots for the rIsdB study are color-coded by each mAb's Hb-blocking status, as determined by BLI, where red—blocker, green—non-blocker, and yellow—partial blocker.

Cell-Based Assays

The binding of human Hb to endogenously-expressed IsdB on *S. aureus* cells was used to assess the blocking effect of a panel of anti-IsdB mAbs as described by Pishchany et al. [15] with the following modifications. The *S. aureus* ΔSpA strain was used. Anti-IsdB mAbs at a concentration of 600 nM were incubated with *S. aureus* cells for 10 min at room temperature before purified human Hb was added to give a final Hb concentration of 150 nM. Detection of Hb was performed by standard Western blotting with a biotinylated primary antibody (sheep polyclonal anti-Hb, biotinylated, Abcam ab95152, used at 2 µg/ml) followed by a streptavidin-conjugated secondary reagent (Streptavidin-IRDye 800 CW, 1 mg/ml; Odyssey 926-32230, 1:4000 dilution). A Lycor Odissey system was used to image the blot and to quantify the band intensities, data were expressed as % of maximum Hb binding in absence of mAbs.

Results and Analysis

Figure 11A:
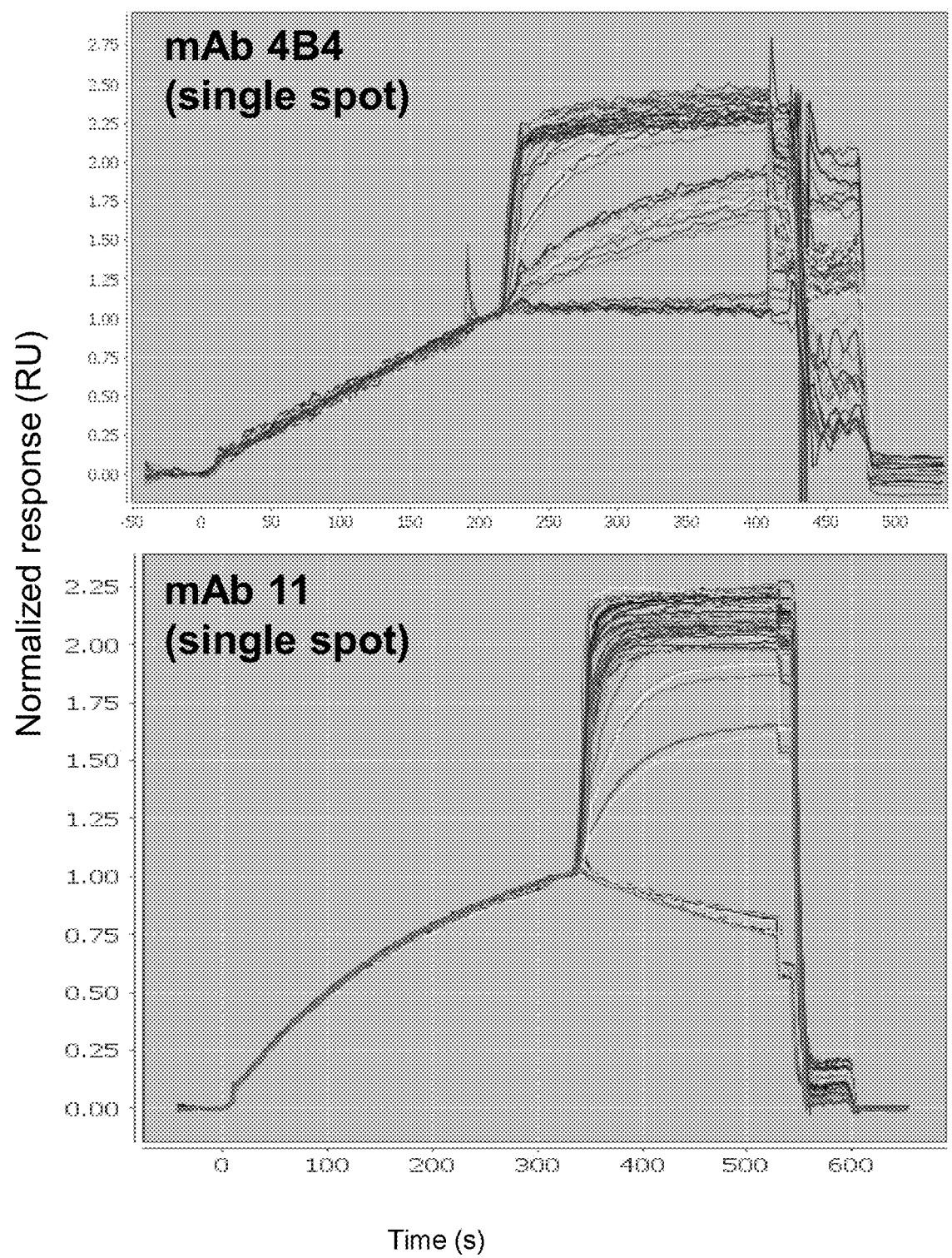
FIGS. 11A-B illustrate examples experimental data collected with a biosensor.
Figure 11B:
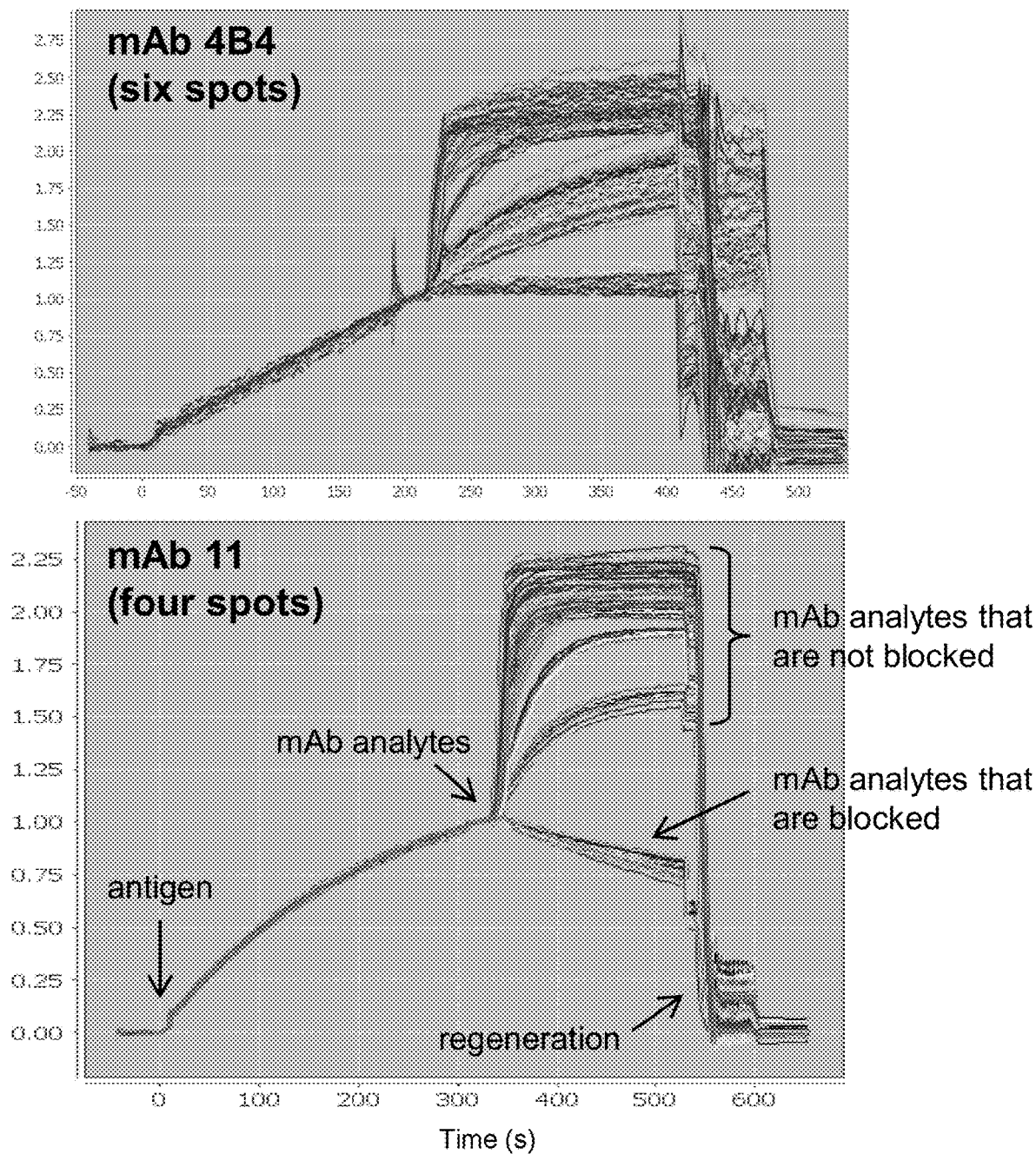

Both the SPRi and BLI platforms are amenable to classical sandwich and premix epitope binning assay formats and the results are concordant and independent of the biosensor platform and the assay format employed. Using the SPRi technology, a series of epitope binning experiments were conducted in a classical sandwich assay format on two panels of mAbs that target unrelated monomeric antigens, namely rhPGRN and rIsdB. Disparate model antigens were chosen to test the general applicability of the present method. Having fewer than 96 mAbs per panel enabled us to test both the spot-to-spot and injection-to-injection reproducibility of the present experiments and to explore various densities of a given mAb ligand within an array. FIGS. 11A-B show data obtained by SPRi for two independent experiments on rhPGRN (panel A) and rIsdB (panel B), in which 96 mAb analytes were injected in succession over a 96-ligand mAb array. For mAbs that were facile to regenerate, data that were reproducible was obtained on individual spots (FIG. 11A) and reproducible across multiple spots that were coupled with the same mAb at different densities (FIG. 11B). The runtime of each experiment that addressed an entire 96×96 analyte-on-ligand interaction matrix was about 30 hours, using standard injection times.

Figure 12:
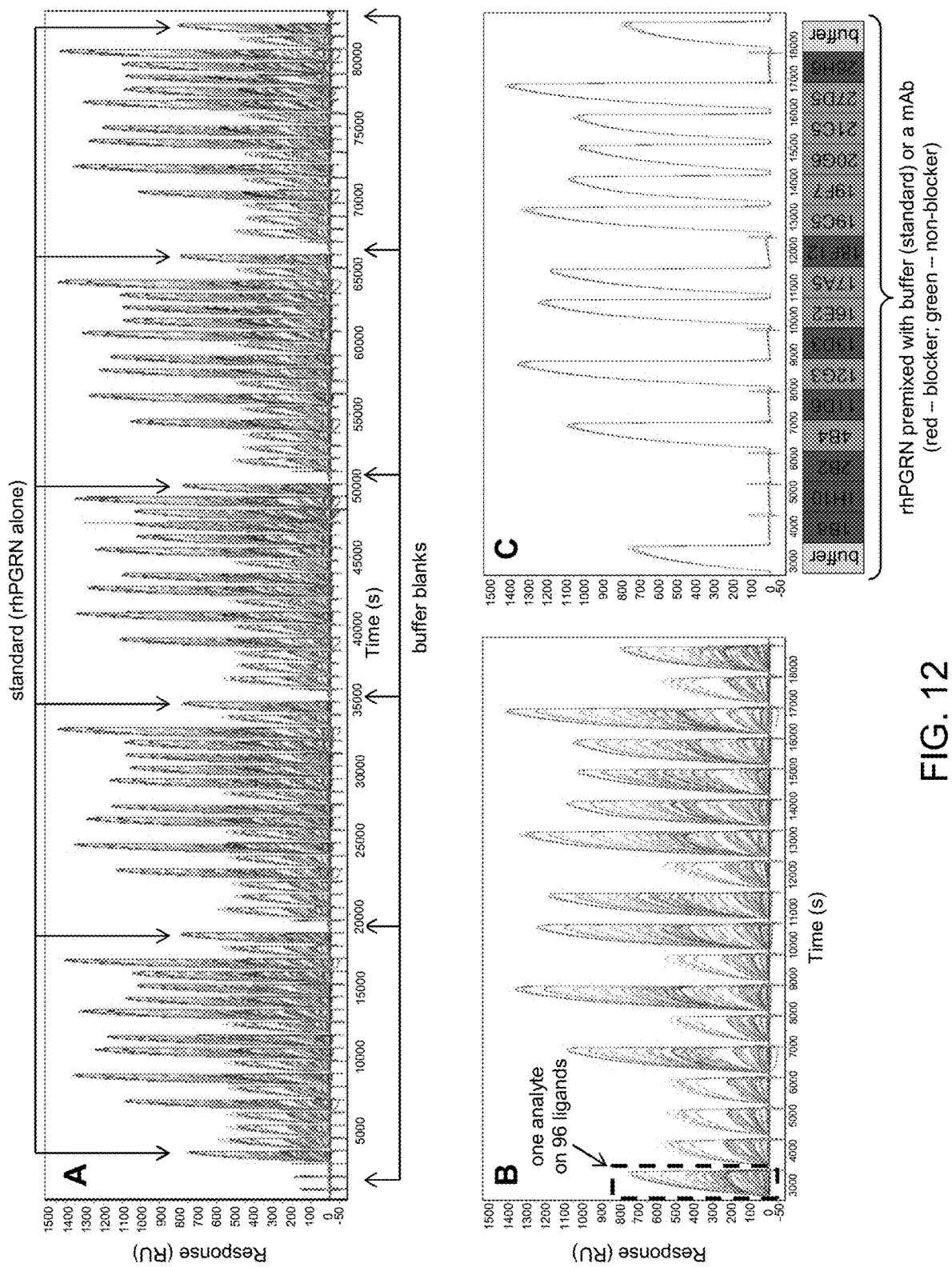
FIG. 12 illustrates example experimental data collected with a biosensor.

The anti-hPGRN mAbs by SPRi was also studied in a premix assay format. FIG. 12, Graph A, shows a concatenated view of the sensorgrams obtained for 96 analytes (i.e., five replicate sets of hPGRN premixed separately with each of the sixteen mAbs, interspersed with samples of rhPGRN alone and buffer blanks) injected over a 96-ligand array, comprising sixteen mAbs coupled onto six spots each. FIG. 12, Graphs B and C, shows an expanded view of the data obtained for the first set of analytes over the entire 96-ligand array (panel B) or over three spots coupled with the same mAb (panel C). For both the classical sandwich and premix assay formats on rhPGRN, the assignment of analyte/ligand mAb pairs as blockers or non-blockers was generally clear-cut, based on the lack of response or an obvious response, respectively.

Figure 13:
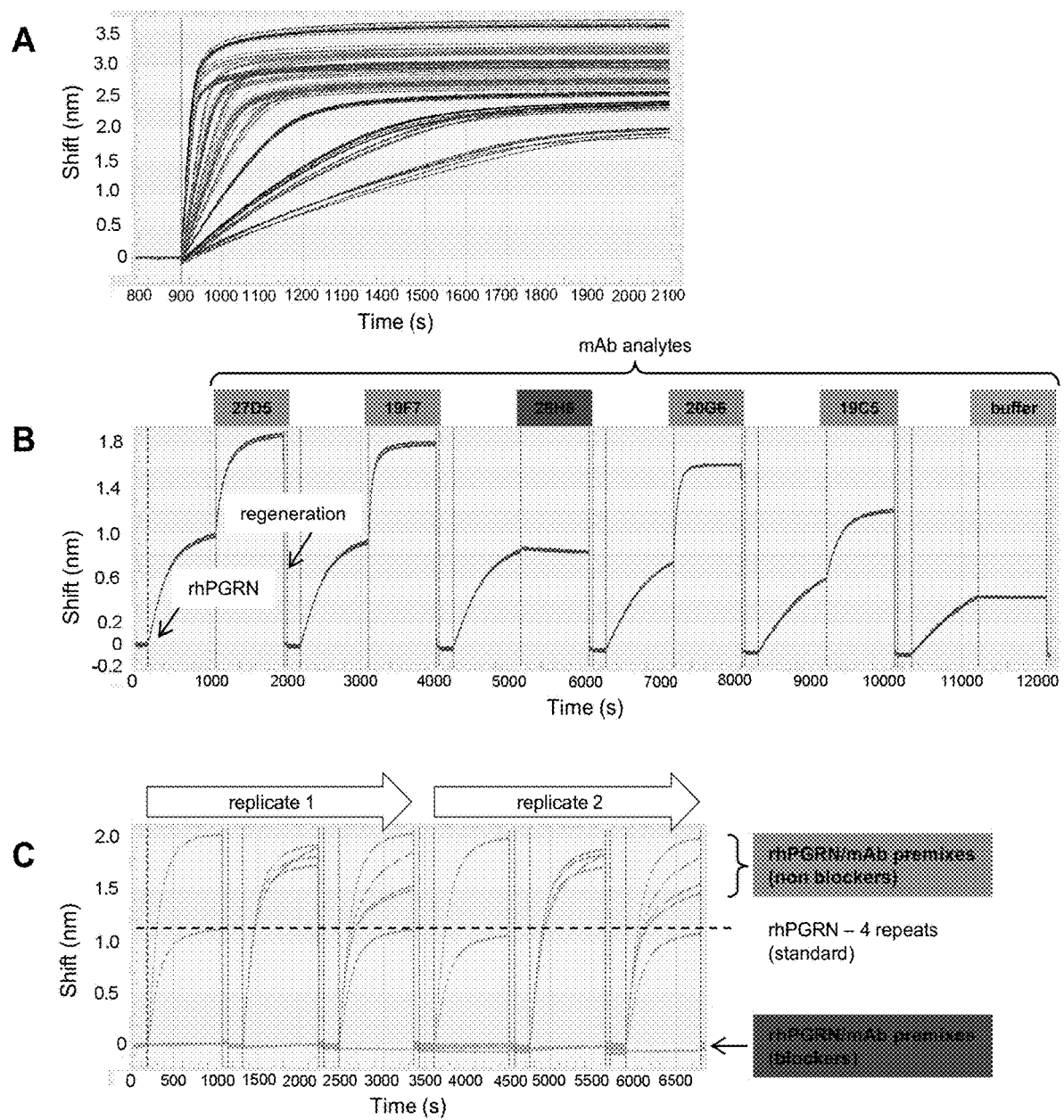
FIG. 13 illustrates example experimental data collected with a biosensor.

A similar epitope binning analysis was performed on rhPGRN using the BLI platform in 96-channel mode. FIG. 13, Graph A, shows an overlay plot for a typical amine-coupling of 96 ligands (i.e., sixteen anti-hPGRN mAbs on six sensors each), highlighting the good sensor-to-sensor reproducibility. FIG. 13, Graph B, shows an example of the sensorgrams obtained for a classical sandwich assay on a 96-ligand mAb array (for clarity, the data for two sensors are shown). A maximum of five different mAb analytes could be run per experiment, as limited by the autosampler's capacity, and since only sixteen mAb analytes were used, all but one of them in three separate experiments was run. To extend the scope of the classical sandwich assay on the BLI to a 96×96 analyte-on-ligand interaction matrix, one microplate can be used to accommodate four mAb analytes (i.e., ninety-six 100 µl-aliquots per mAb analyte) and the second microplate can be dedicated to common reagents (i.e., antigen, buffer, and regeneration solutions). As a result, 24 separate experiments would be run if the reagent plate is re-used, while the sample plate is exchanged for one that accommodates a new set of four mAb analytes until all 96 mAb analytes are addressed, thereby totaling twenty-four 384-well plates of mAb analytes. Not only is this cumbersome, evaporation would limit the number of times the reagent plate could be re-used.

The BLI's unique dip-and-read format enables the parallel analysis of a diverse set of interactions because analyte/ligand pairs are entirely independent of one another. To demonstrate this versatility, a premix assay was performed on the same panel of sixteen anti-hPGRN mAbs in an hour by coupling each mAb onto six sensors and dipping all 96 mAb-coated sensors into samples of rhPGRN premixed with a mAb; rhPGRN without any premixed mAb served as the "standard" against which responses of the premixes were compared on a per sensor (i.e., ligand) basis. Three binding cycles in 96-channel mode therefore addressed all 256 pairwise permutations that are run to test each mAb as both analyte and ligand along with duplicates of the standard. Assigning analyte/ligand mAb pairs as blockers or non-blockers was straightforward due to the high quality of the BLI data, as shown in FIG. 13, Graph C.

Figure 3A:
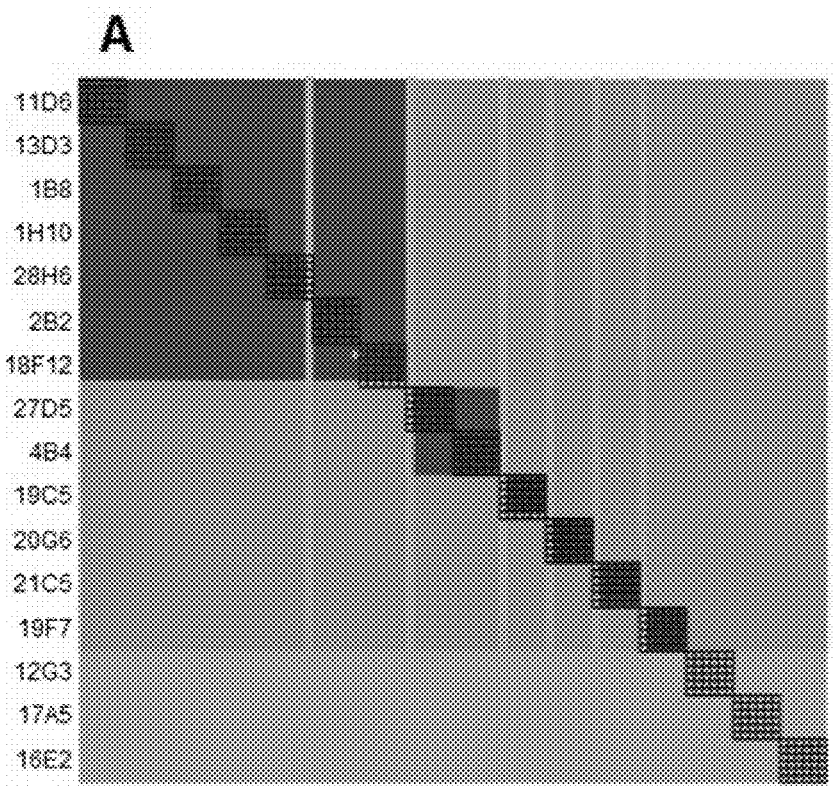
FIGS. 3A-D illustrate example heat maps of antibody interactions.
Figure 3B:
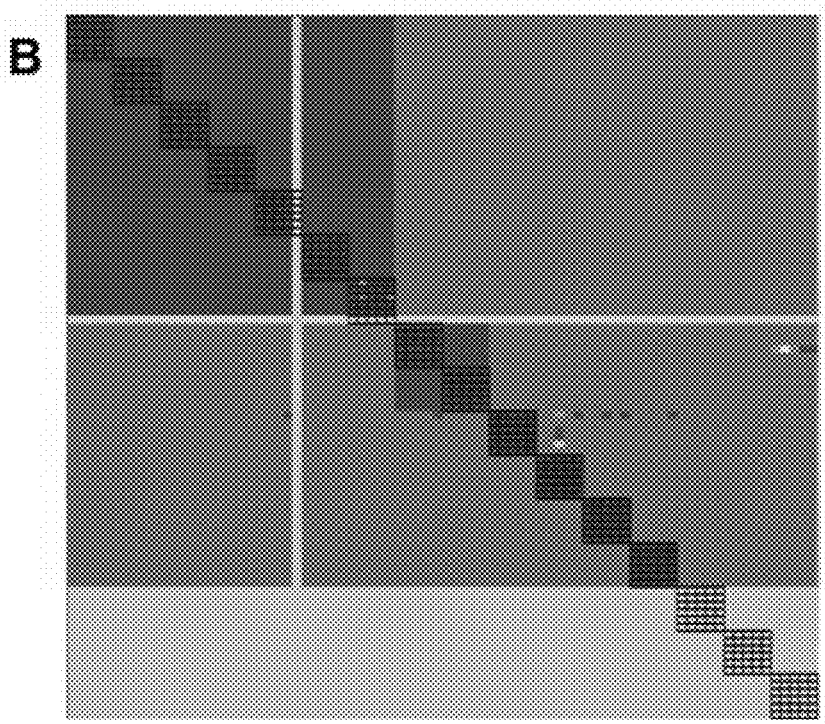
Figure 3C:
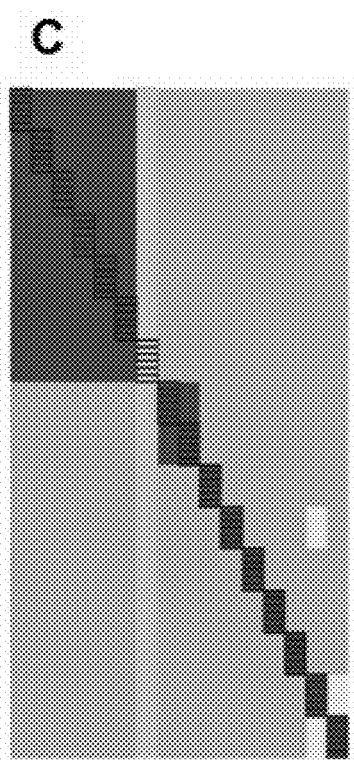
Figure 3D:
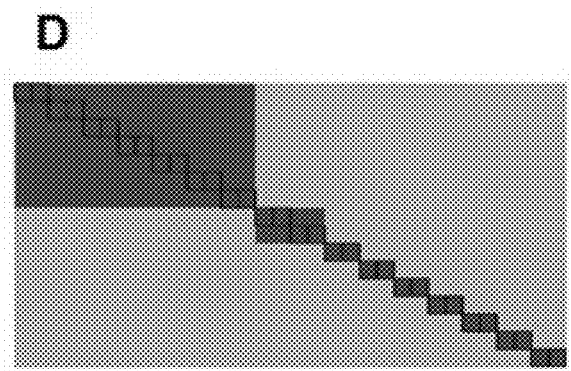
Figure 3E:
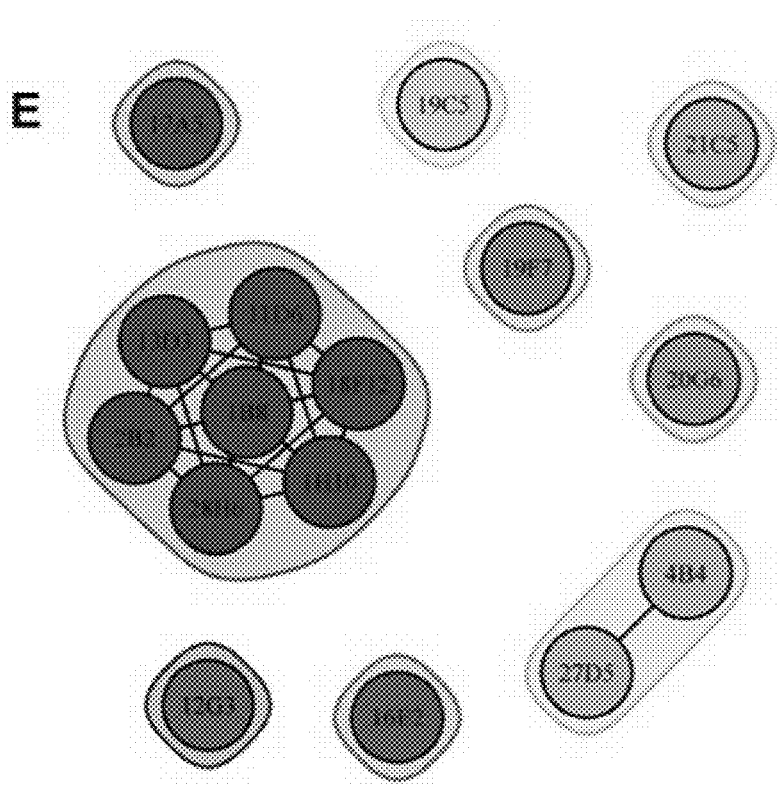
FIG. 3E illustrates an example node plot of antibody interactions.

FIGS. 3A-D summarizes the epitope binning results obtained for the four experiments described above on rhPGRN. Since the SPRi experiments were each conducted as a 96×96 analyte-on-ligand interaction matrix (FIG. A and FIG. 3B), the blocking status of each mAb pair was tested multiple times. For example, to study a panel of sixteen mAbs in a classical sandwich assay format, each mAb was arrayed onto six spots and injected each mAb analyte six times, thereby testing every mAb pair for cross-blocking 72 times and every self-blocking interaction 36 times. Fewer than 72 cross-blocks and 36 self-blocks are shown for some mAb pairs because some injections (i.e., analytes) and spots (i.e., ligands) were excluded from the heat map due to poor quality data. Due to BLI's significantly lower unattended throughput and higher analyte consumption, each mAb analyte was analyzed once (FIG. 3C) or twice (FIG. 3D), respectively on a 96-ligand array. FIG. 3E shows a graphical representation of the epitope bins as a node plot determined from both assay formats using both technologies. Node plots can be interpreted by following some simple rules. It is assumed that all mAbs within a node plot have been tested comprehensively for pairwise blocking against one another. Therefore, a chord between two mAbs indicates a blocking relationship and no chord indicates no blocking. Epitope bins are inscribed by the envelopes. As indicated by the nine separate groupings, the sixteen anti-hPGRN mAbs fell into nine non-overlapping bins, i.e., no bin blocked any other bin such that a sandwich pair could be formed across any two bins. Seven mAbs were in unique bins by themselves, while the remaining nine mAbs were divided over two additional bins. Taken together, these results demonstrate that the same binning outcome was obtained regardless of the biosensor platform used or the epitope binning assay format employed.

Figure 4A:
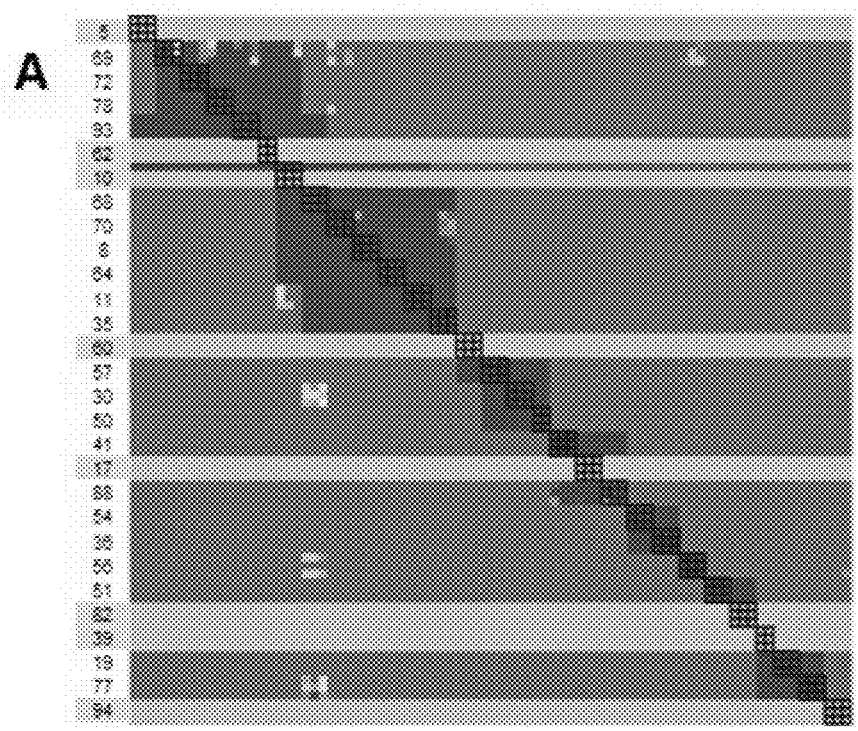
FIGS. 4A-C illustrate example heat maps of antibody interactions.
Figure 4B:
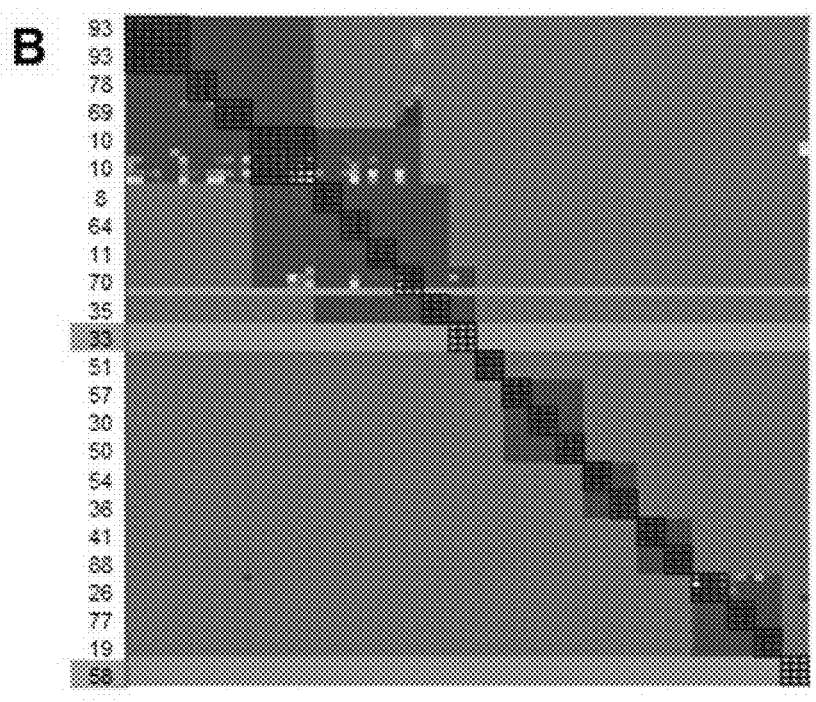
Figure 4C:
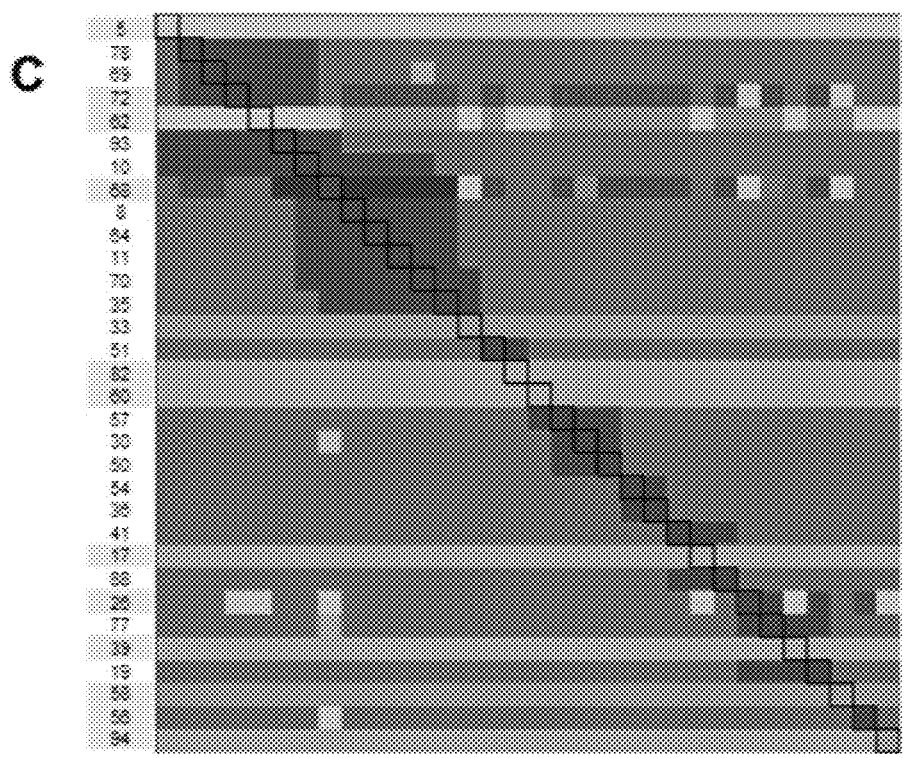
Figure 4D:
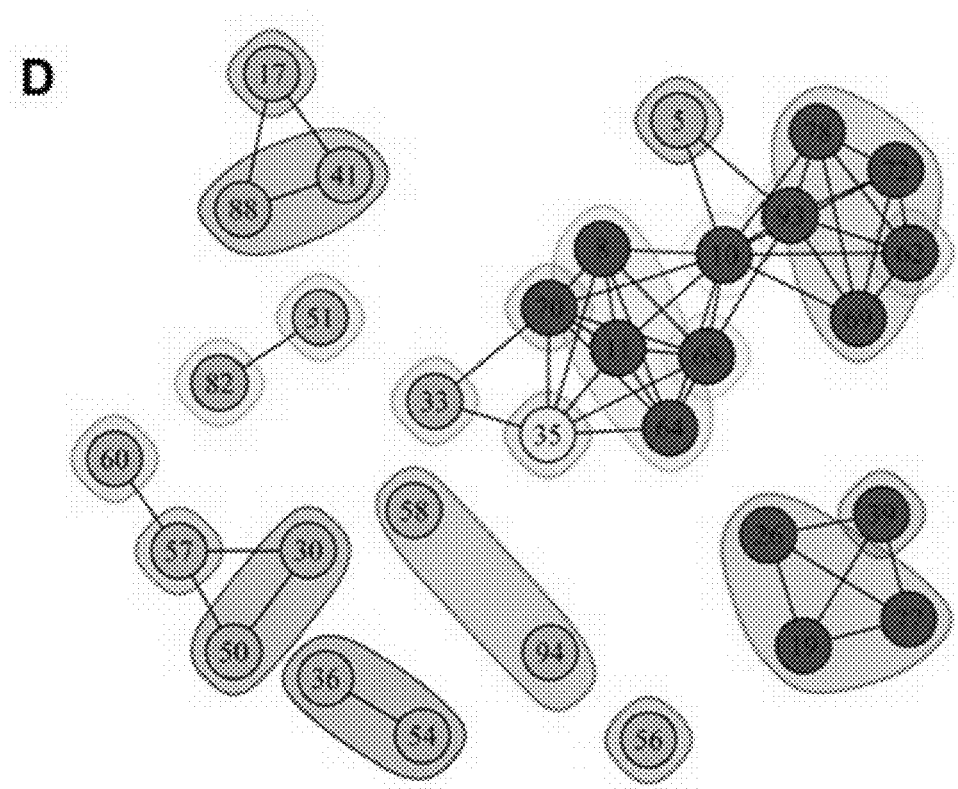
FIG. 4D illustrates an example node plot of antibody interactions.

Additionally, it is noted that high-throughput epitope binning assays yield exceptional resolution of epitope bins. Unlike the present study of anti-hPGRN mAbs described above, the present epitope binning experiments on a panel of 63 unique anti-IsdB mAbs (analyzed as smaller, intersecting subsets as summarized in FIGS. 4-9) revealed a high frequency of bins that overlapped with other bins and therefore provided a model system for demonstrating how high-throughput binning can yield exquisite discrimination of epitopes. FIG. 4A shows the heat map for 29 mAbs, each analyzed in triplicate as both analyte and ligand. Seven of these mAbs were inactive as ligand on all three spots tested; mAb 10 was inactive on two of the three printed spots (inactive ligands are shown by the grey rows). FIG. 4B shows the heat map for an independent experiment on 22 unique mAbs, comprising 19 mAbs that had been active as ligand in the previous experiment and three additional mAbs (26, 33, and 58). Twenty of these mAbs were printed onto four spots each and two of them (mAbs 10 and 93) were printed onto eight spots each to complete a 96-ligand array. FIG. 4C shows the merged heat map for the 32 unique mAbs tested across these two experiments and FIG. 4D shows a node plot that represents the deduced epitope bins and their inter-bin relationships. Orphan analytes—mAbs that were inactive as ligand (i.e., 5, 17, 33, 39, 58, 60, 62, 82, and 94, as shown by the grey rows)—introduce gaps into the heat map because they were neither tested for self-blocking nor cross-blocking against one another. While tentative bins can be assigned to the orphan analytes based on their blocking against the active ligands, further experiments would be carried out to determine whether the missing orphan/orphan cross-blocking information would alter those assignments; thus, each orphan is inscribed by its own envelope. Orphans 58 and 94 were assigned to the same bin because they exhibited the same blocking profile, i.e., they were not blocked by any ligand, but there is no chord between them because their ability to block one another was not determined. Thus, 32 mAbs to 21 epitope bins were assigned. All node plots for anti-IsdB mAbs are color-coded according to each mAb's functional activity, as determined by their ability to block (red), or not block (green), rIsdB's binding to Hb, which is the natural ligand for native IsdB, discussed later.

Figure 5A:
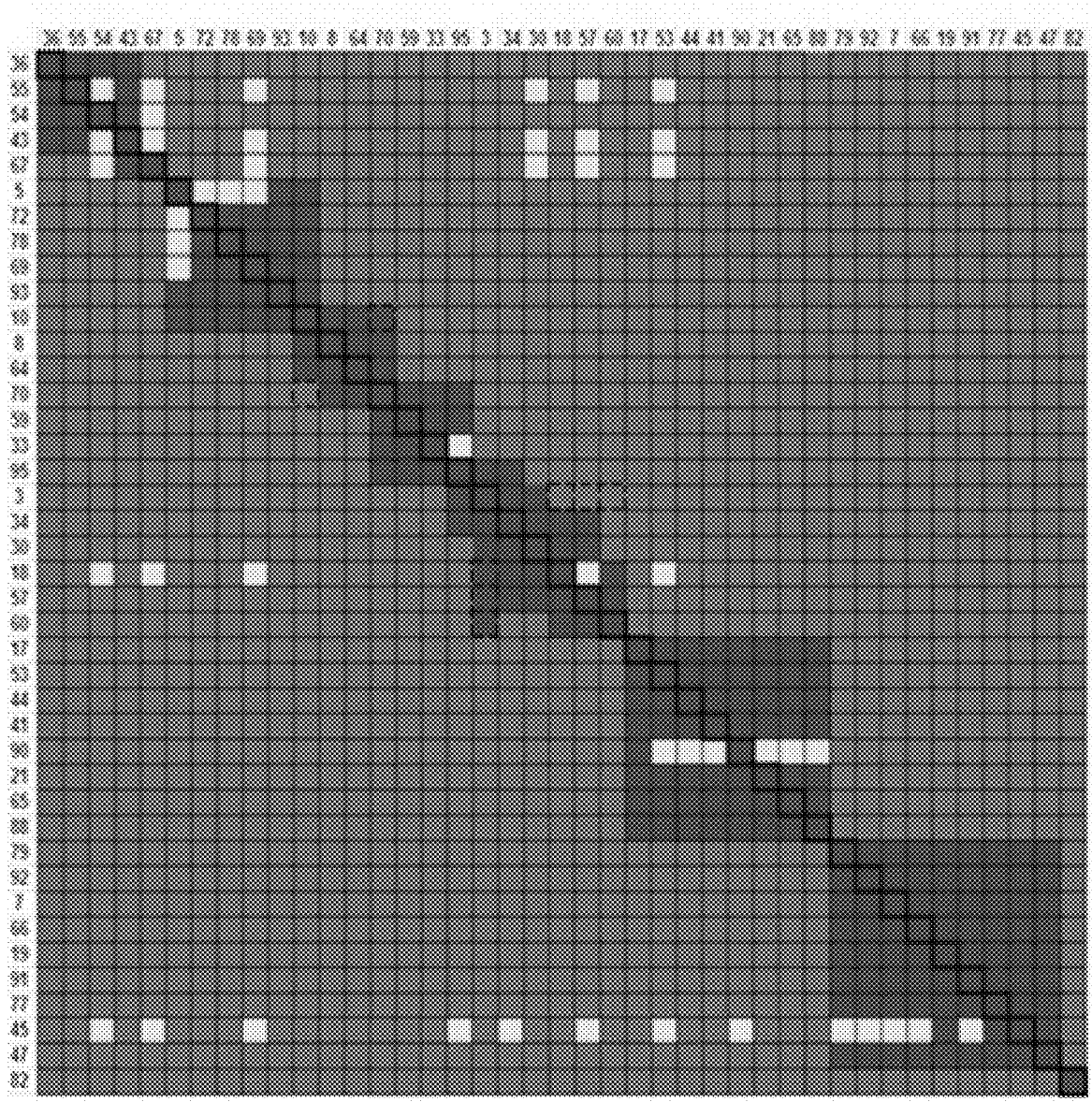
FIG. 5A illustrates an example heat map of antibody interactions.
Figure 5B:
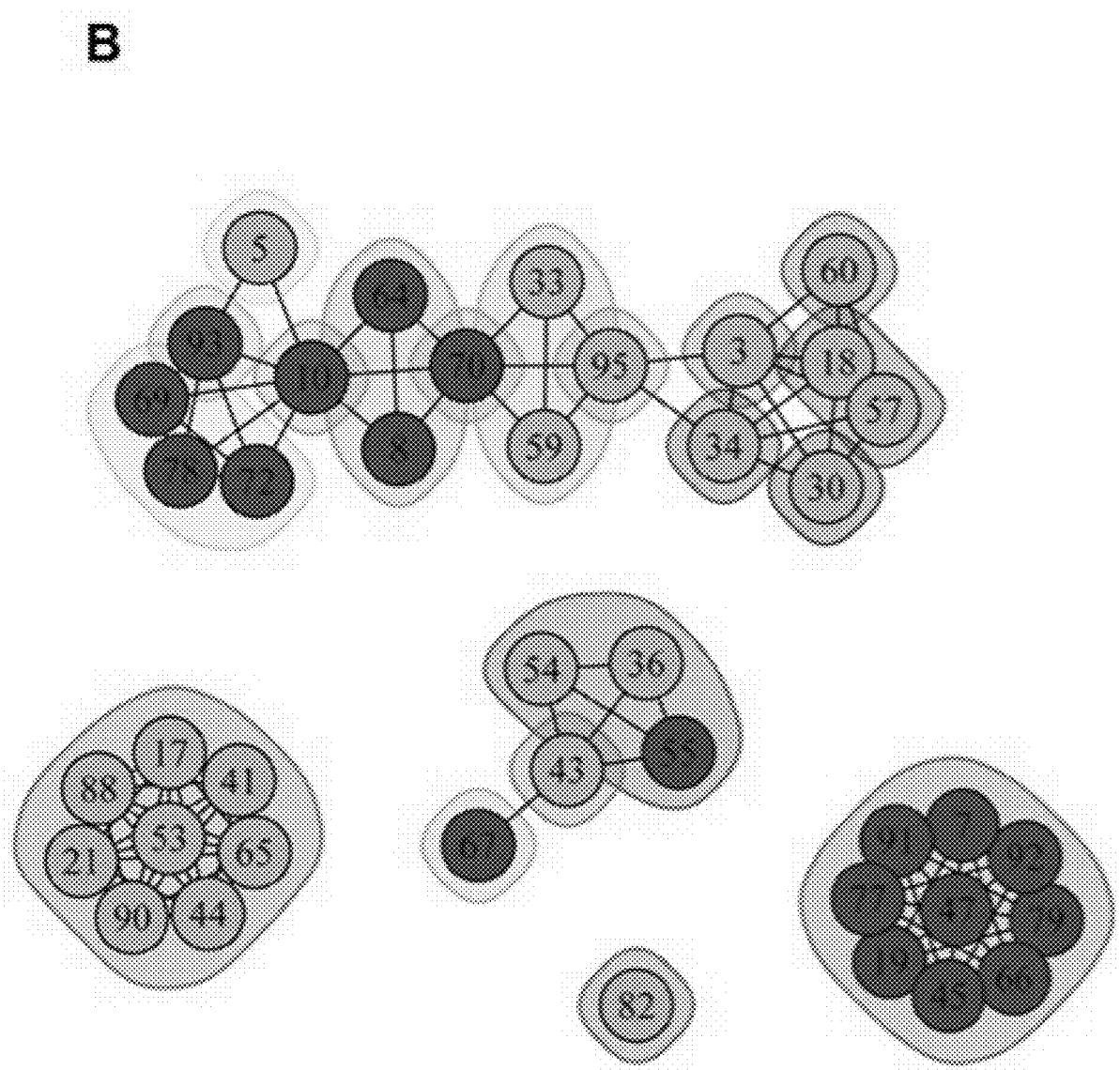
FIG. 5B illustrates an example node plot of antibody interactions.

This analysis of the present anti-IsdB mAbs was extended to a larger panel comprised of 41 mAbs (some of which were also represented in FIG. 4) and performed a classical sandwich assay on them by BLI. To minimize ligand attrition and thus increase the confidence of the bin assignments, the regeneration solution was tailored to the individual coupled mAbs, which is a unique and significant advantage of the BLI approach because sensors are not linked to one another and they dip into discrete sample wells. FIGS. 5A-B shows the results of this analysis represented as both a heat map (panel A) and a node plot (panel B). Examining the heat map shows that some pairings gave an ambiguous result in both directions (e.g., 54/67, 5/69, 5/72, and 5/78, indicated by the yellow cells), while other pairings gave a conflicting result dependent upon the order of addition (e.g., 10/70, 3/18, 3/57, and 3/60, indicated by the cells with a dotted border). Both scenarios introduce uncertainty into the bin assignments and warrant further experiments to clarify the result. In the case of a conflicting blocking result between two mAbs, these were connected with a chord in the node plot because a blocking relationship was observed, even if it was only in one direction of the heat map. In this example, 41 mAbs to 19 epitope bins were assigned. Of these bins, only three did not block any other bin, while the remaining mAbs fell into two clusters, one of which represented an intricate network of bins.

Figure 6A:
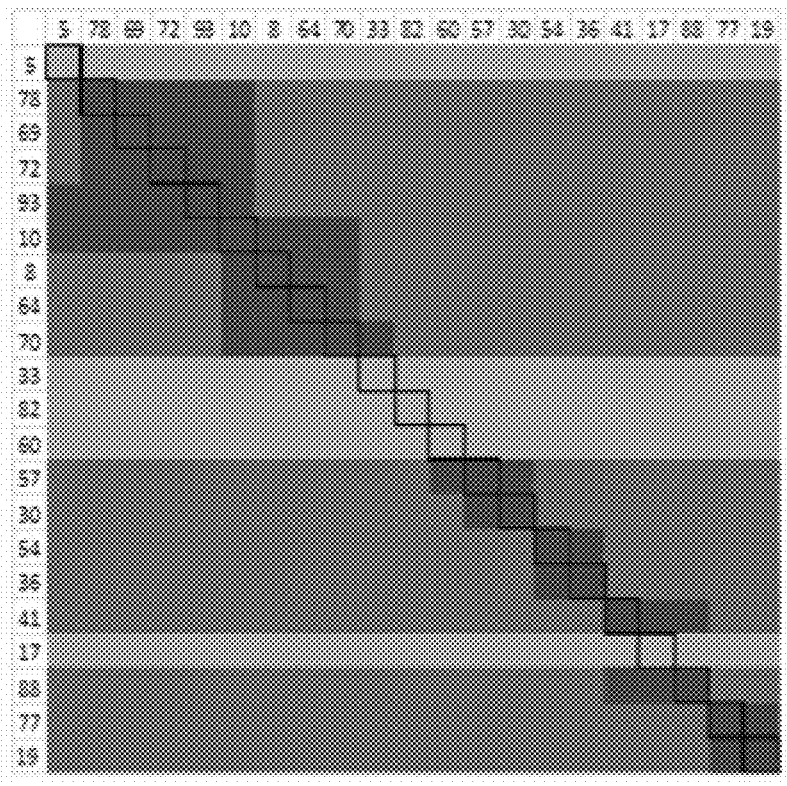
FIGS. 6A-B illustrate example heat maps of antibody interactions.
Figure 6B:
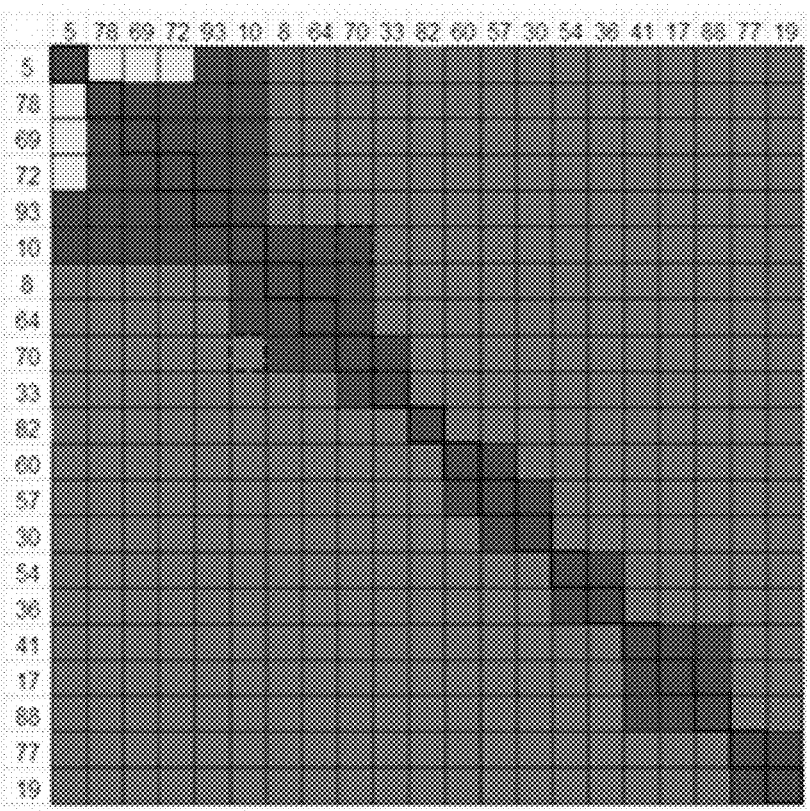
Figure 6C:
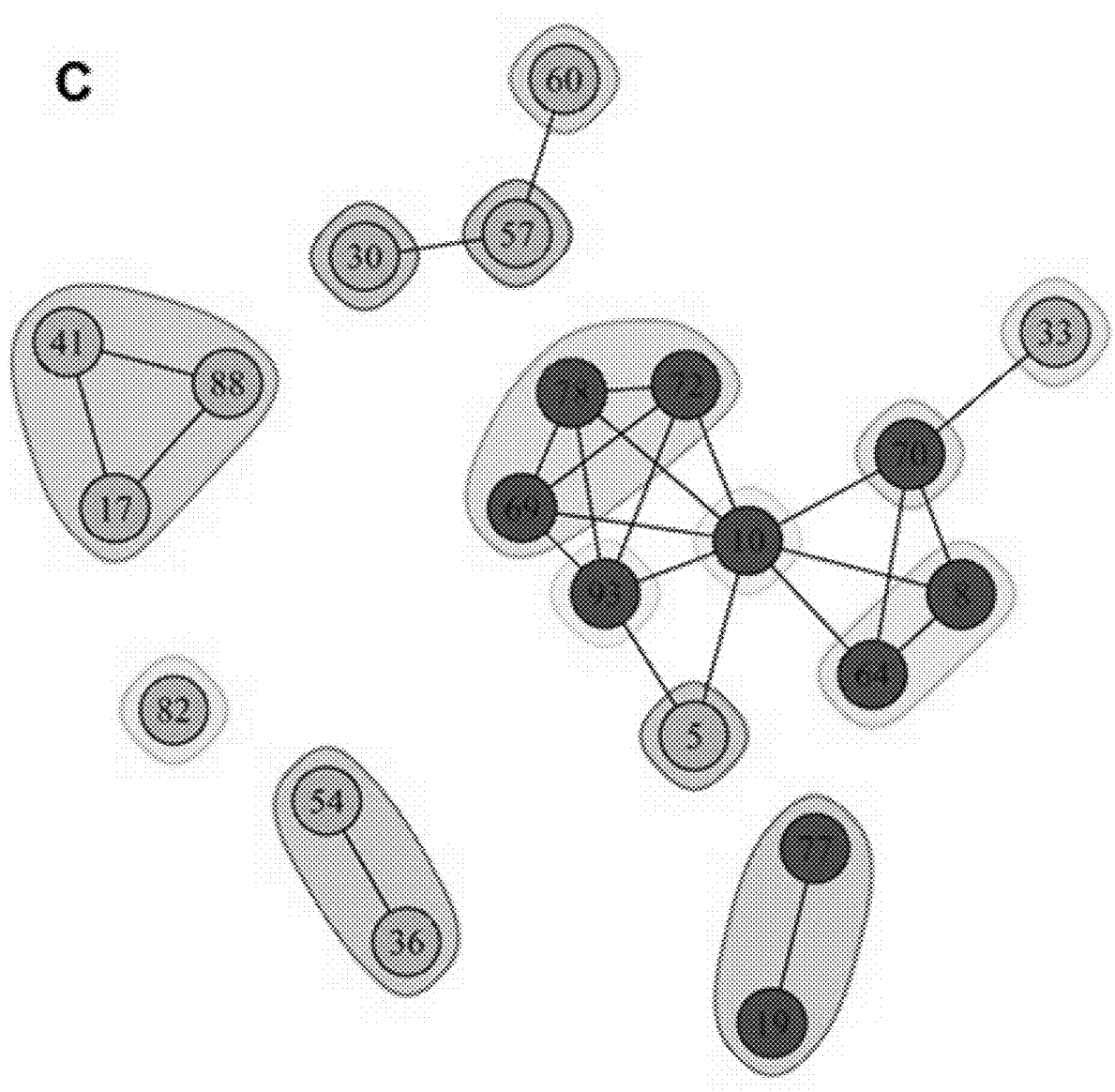
FIG. 6C illustrates an example node plot of antibody interactions.

To facilitate a direct comparison of the results obtained for classical sandwich assays on the two biosensor platforms, FIGS. 6A-B is provided to show the heat maps for 21 mAbs that were represented in both experiments (panel A—SPRi and panel B—BLI). FIG. 6C shows the deduced node plot. It is noteworthy that five ligands (5, 17, 33, 60, and 82) were inactive by SPRi but active by BLI. Their activity was preserved in the BLI assay because a gentler regeneration condition was employed relative to that used for most of the other ligands (i.e., 15 mM phosphoric acid instead of 75 mM phosphoric acid). Thus, the open configuration of the BLI platform enabled us to minimize ligand attrition by tailoring the regeneration condition per mAb-coated sensor, whereas the SPRi's single flow cell approach relied on the use of a universal regeneration condition for a given ligand array which damaged some ligands.

Figure 7A:
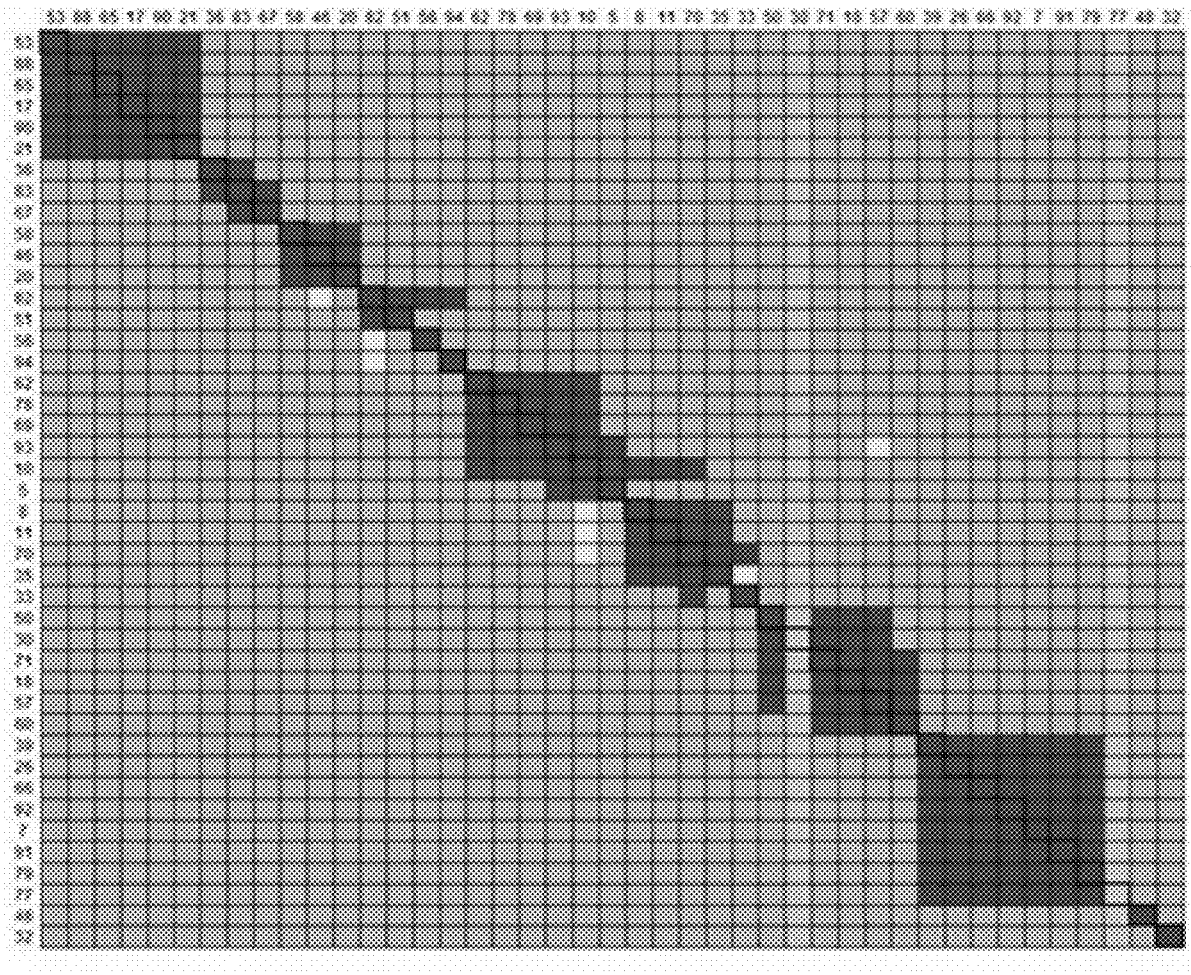
FIG. 7A illustrates an example heat map of antibody interactions.
Figure 7B:
FIG. 7B illustrates a black and white alternative to using colored heat map blocks.
Figure 7B:
Figure 7B:
Figure 7C:
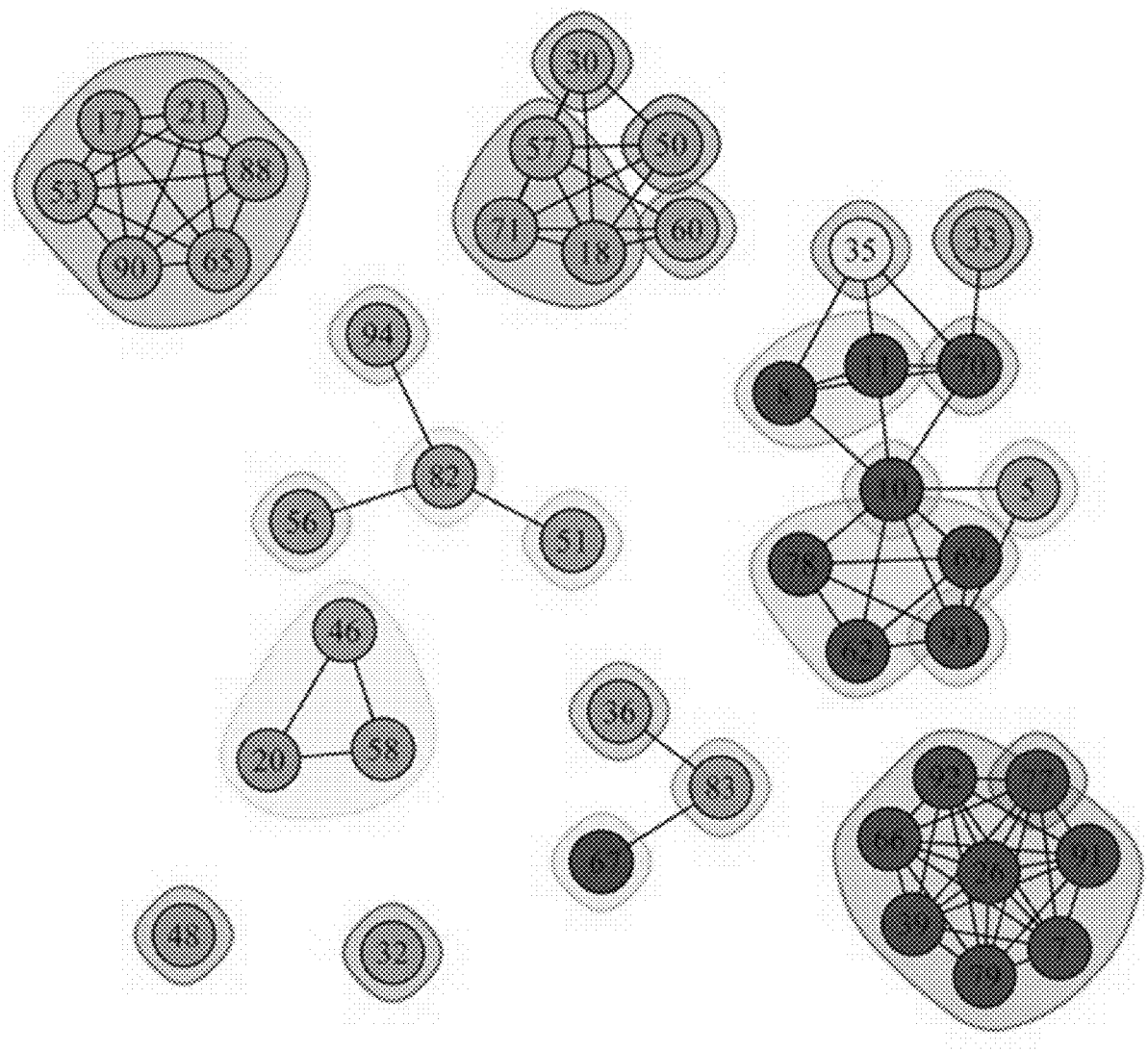
FIG. 7C illustrates an example node plot of antibody interactions.

Furthermore, the BLI platform allows for ad hoc sensor replacement and on-line reloading of an array, which makes the in tandem epitope binning assay format feasible. Essentially, to complement the classical sandwich data and explore an alternate way of minimizing ligand attrition, in a tandem epitope binning assay was performed on 43 unique anti-IsdB mAbs using BLI. By employing a reversible capture of the antigen via a pre-immobilized anti-His mAb, neither the antigen nor the mAbs were regenerated, which preserved the native activity of the reagents (one only may need to know how to regenerate the capture surface, which is often well-established). FIGS. 7A-C provides information regarding an overlay plot of the sensorgrams obtained for mAb 69 binding as analyte to anti-His captured antigen that was first saturated by an array of 48 mAbs (representing 43 unique clones); in this case, mAb 69 is clearly blocked only by mAbs 10, 62, 69, 78, and 93. Specifically, FIG. 7A shows the heat map for a comprehensive pairwise analysis of 43 mAbs As mentioned previously, FIG. 7B illustrates alternative black and white blocks that can be used to replace colored heat map blocks. FIG. 7C shows a node plot of the bin assignments. Neither mAb 30 nor mAb 77 were tested as analyte due to their low sample availability, so are "orphan ligands" in this assay. While these two mAbs were not tested for mutual cross-blocking, there is sufficient information from the heat map to assign them to different bins. The BLI's autosampler limited an unattended run to only eight mAb analytes (since each mAb analyte was distributed into 48 wells of the sample plate), so six separate experiments were generated to address a full 48×48 interaction matrix when the instrument was used in 96-channel mode.

Figure 8A:
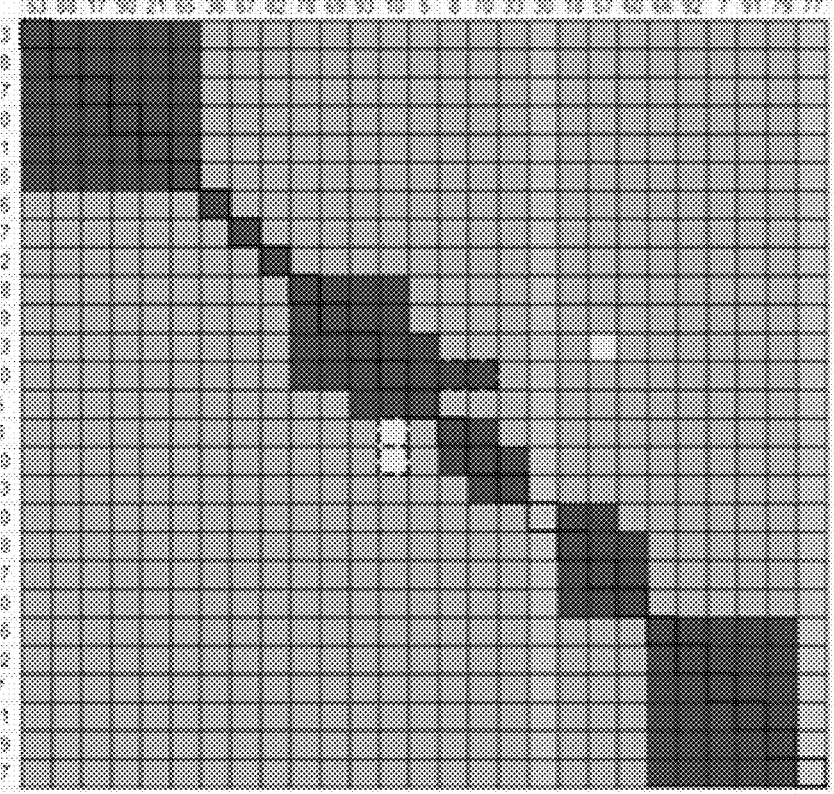
FIGS. 8A-B illustrate example heat maps of antibody interactions.
Figure 8B:
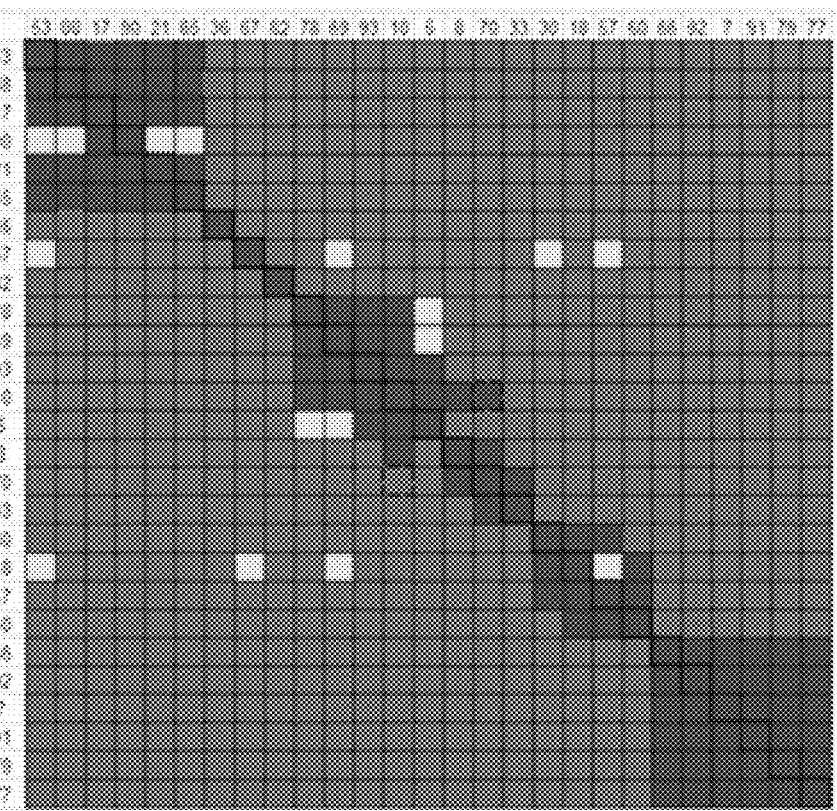
Figure 8C:
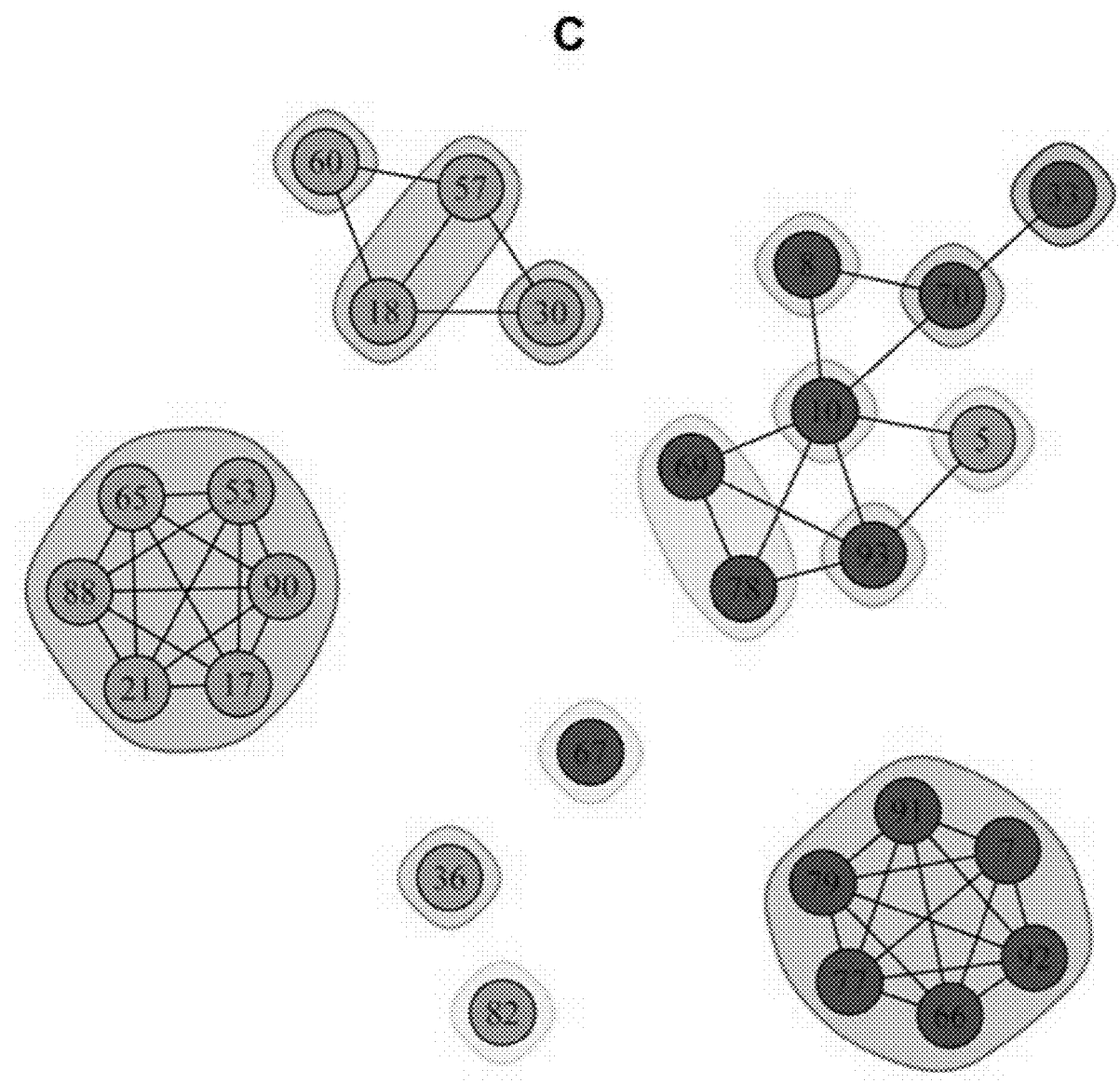
FIG. 8C illustrates an example node plot of antibody interactions.
Figure 9A:
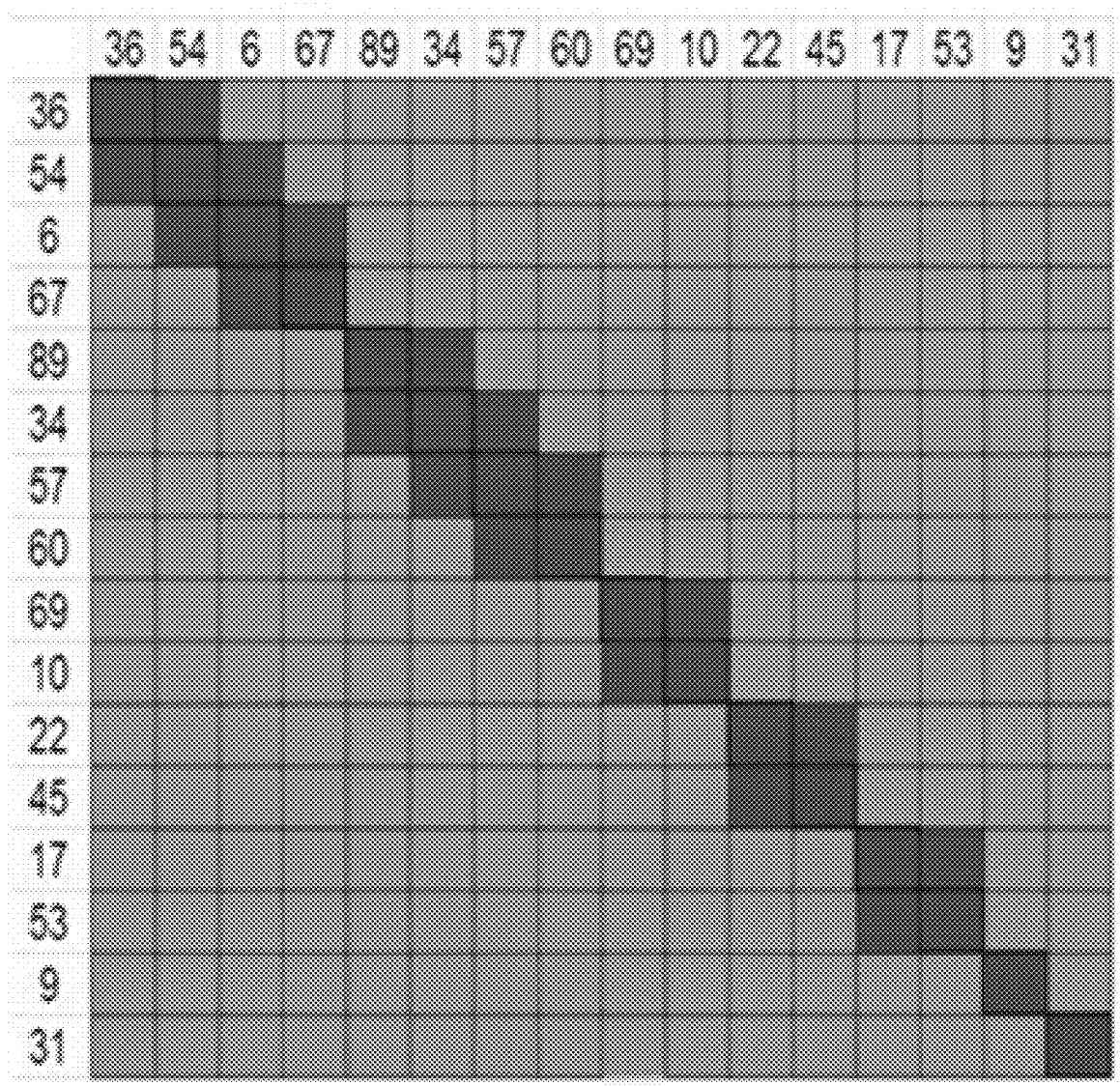
FIG. 9A illustrates an example heat map of antibody interactions.
Figure 9B:
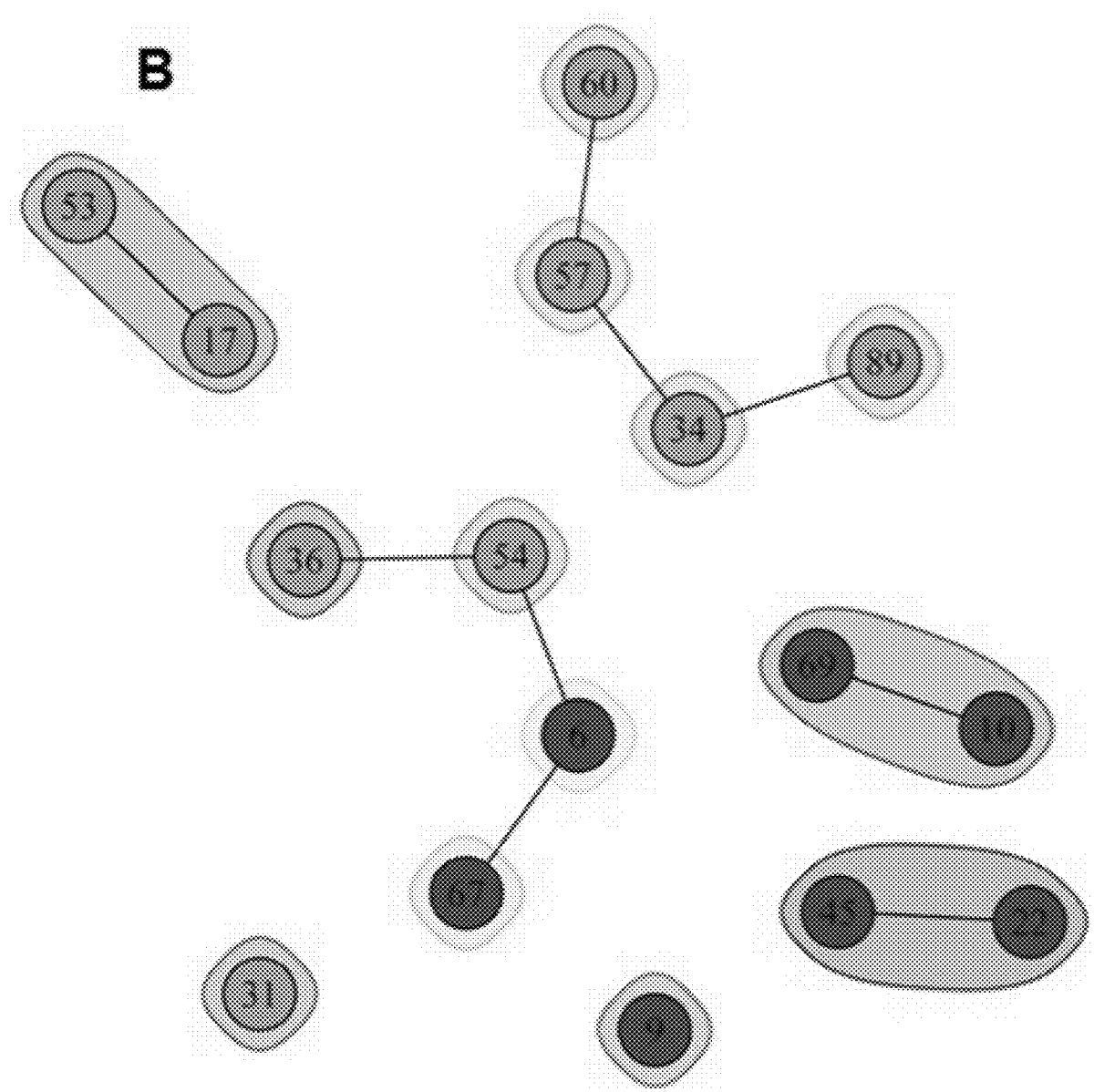
FIG. 9B illustrates an example node plot of antibody interactions.

FIGS. 8A-C shows a direct comparison of the heat maps obtained for 27 anti-IsdB mAbs that were represented in both assay formats using BLI (panel A—classical sandwich and panel B—in tandem). The same node plot (panel C) was deduced irrespective of the assay format used. An tandem style epitope binning experiment was also performed on sixteen carefully selected anti-IsdB mAbs to demonstrate that a small panel of mAbs can yield overlapping bins if it contains sufficient epitope diversity (FIG. 9A). Thirteen epitope bins were deduced (FIG. 9B), regardless of whether an anti-His or anti-Flag capture of the antigen (data not shown) was employed, confirming that neither of the two immobilization methods perturbed the epitopes within mAb panel.

Epitope bins also can correlate with functional activity. Hb is the natural ligand for IsdB. Using the BLI platform, 63 unique anti-IsdB mAbs were screened to determine whether they blocked Hb binding and then chose a smaller subset on which a functional cell-based blocking assay was performed. It was observed that a strong correlation between the present Hb-blocking data is obtained on recombinant and native IsdB, i.e., of the sixteen mAbs tested in a cell-based assay, only one blocking result conflicted with the biosensor determination (when tested once in a cell-based assay, mAb 77 was assigned as a non-blocker because it gave only 20% reduction in Hb binding, but was a clear blocker when tested multiple independent times in the biosensor assay). All the node plots in the present rIsdB study (see FIGS. 4-9) are color-coded according to each mAb's ability to block the rIsdB/Hb interaction, as determined by BLI. The results reveal an excellent correlation between epitope bin and Hb-blocking activity, i.e., all mAbs in a given epitope bin or cluster of inter-connected epitope bins exhibited the same blocking profile towards Hb. Moreover, several independent epitope bins showed functional activity, suggesting that mAbs with different epitopes may block Hb via different mechanisms of action. It is noteworthy that mAb 35, which cross-blocks a set of Hb-blockers (mAbs 8, 11, 64, 68, and 70) and a Hb-non-blocker (mAb 33), as shown in FIG. 4D, appeared to "partially block" Hb (data not shown).

There are also several advantages of the SPRi platform, including its exceptionally low sample requirement, facile sample preparation, and exceptional unattended throughput. In evaluating two 96-ligand array-based technologies, it was found that they were complementary to one another. One of the main advantages of using single flow cell microarray-based SPRi is its exceptionally low sample consumption, which is not only appealing for conserving precious samples, but simplifies the sample preparation. Since similar mAb concentrations were used on both platforms, sample consumption can be compared in terms of volume. While both platforms use only 100 µl per mAb to array 96 ligands, the SPRi platform consumes almost 100-fold less mAb analyte than the BLI platform to perform a comprehensive epitope binning experiment on 96 mAbs. Thus, the SPRi assay consumes a single 120 µl per mAb analyte, whereas BLI uses 10 ml per mAb analyte because it is distributed as ninety-six 100 µl-aliquots into a 384-well sample plate. Another significant difference between the SPRi and BLI platforms is their unattended throughput, as dictated by their respective autosamplers. The SPRi platform has unparalleled unattended throughput because 96 analytes can be injected over a 96-ligand array, thereby addressing more than 9,200 analyte/ligand interactions per experiment, with a runtime of approximately 30 hours. In contrast, the number of analytes that can be tested by BLI against a 96-ligand array in the context of an epitope binning experiment is limited to five or less, depending upon the assay format used, since all samples (including analytes and common reagents such as antigen, buffer, and regeneration solutions) are accommodated within two 384-well microplates. A higher unattended throughput can be achieved by integrating the BLI system to a robot that automates multi-plate analyses, but this comes at an additional cost to the user. However, even with a robotic system, the unattended runtime of a BLI assay is still limited because of sample evaporation issues.

The BLI platform is highly versatile and enables the parallel analysis of 96 (or other large number of) independent analyte/ligand pairs, ad hoc sensor replacement, and on-line reloading of an analyte- or ligand-array. The open configuration of the BLI platform makes it amenable to the analysis of diverse interactions and various assay formats. Processing a collection of discrete sensors in parallel allows for the simultaneous analysis of 96 entirely independent analyte/ligand interactions in this specific device, which can be exploited to expedite the binning analysis of small panels of mAbs. For example, it was demonstrated that a 16×16 interaction matrix can be addressed using a premix assay format in an hour (or less) using just three binning cycles in 96-channel mode (FIG. 13C). Indeed, the largest panel that can be studied in a single BLI experiment when used in 96-channel mode (without robotic integration) is 23 mAbs, if a premix format is used, because it utilizes only three steps per binding cycle; buffer baseline, analyte binding, and regeneration. Thus, to address an entire 23×23 interaction matrix, each mAb would be coupled onto four sensors and the premixed samples, buffer, and regeneration would be distributed in an appropriate manner across the two sample plates. While this would utilize a complicated sample layout, the runtime would be only an hour if a ten-minute binding cycle was used, since the assay would be complete in just six binding cycles. In contrast, performing a similar analysis using SPRi would take several hours using standard injection times. Another appealing feature of BLI is its ability to load an array on-line, which makes BLI amenable to the in tandem binning assay format. BLI also enables the ad hoc replacement of sensors and various tip types can be processed in parallel to diversify the assay further.

Furthermore, the larger the panel of mAbs in an epitope binning assay, the higher the potential resolution power of the assay. For example, a given antigen may present a very high (theoretical infinite) number of epitopes. The number of unique mAbs that can bind a given epitope is also potentially very high. Given the vast number of possible epitope/mAb pairs that can be generated within a given project, it is helpful early in the discovery of therapeutic mAbs to organize mAbs into epitope bins to narrow down the number of candidates that are studied further in other assays. The rIsdB study highlights that cross-blocking of two mAbs may be notable, but may not be sufficient in information for them to truly belong to the same bin. While the maximum number of bins that can be determined in a given epitope binning experiment is equal to the number of mAbs in the test panel, in practice, a large panel of mAbs often yields fewer bins than the theoretical maximum. The number of bins that can be determined experimentally for a given panel of mAbs is a relative number and depends on both the number and epitope diversity of mAbs being tested. For example, a total of 63 unique anti-IsdB mAbs were tested as intersecting subsets in the experiments shown in FIGS. 4-9 and a different number of epitope bins was deduced in each case. Taking a specific example, when tested within a panel of sixteen mAbs, mAbs 10 and 69 appear to belong to the same bin (FIG. 9B), but their epitopes can be discriminated when tested within a larger panel of 27 mAbs (FIG. 8C) because it includes three mAbs (5, 8, and 70) that block mAb 10 but do not block mAb 69.

In general, only a small number of the total discovered epitope bins in a given project will be functionally relevant. Therefore, one of the benefits to this approach is rapid triaging of a large panel of mAbs early in the discovery process. MAbs within a functional bin can be prioritized based on other important characteristics like biophysical properties, high specificity for the target and species cross-reactivity for the same target (e.g., mouse, cynomolgus monkey, and human). The present study has demonstrated that label-free epitope binning assays that are both high-throughput and high-resolution can guide discovery and development of therapeutic mAbs.

What is claimed is:

1. A method of sensing and characterizing antibody blocking interactions, comprising:
    physically contacting antibodies contained in a fluid over a label-free biosensor wherein the biosensor is controlled via a graphical interface;
    identifying blocking interactions, including cross-blocking, of the antibodies in the fluid using the label-free biosensor to sense the blocking interactions and a processor to generate interaction profiles for the antibodies;
    assigning, using the processor, the antibodies to one or more bins, wherein the antibodies sharing a common blocking interaction profile are assigned to a common bin and each antibody is only assigned to one bin;
    displaying nodes, via the graphical interface, grouped together representing antibodies in a common bin; and
    displaying connections, via the graphical interface, between at least a portion of the nodes, wherein the connections include blocking interactions between the antibodies including multiple connections, individual connections, or both, and wherein a portion of the connections connect at least one antibody to a plurality of other antibodies.

2. The method of claim 1, wherein the antibodies are monoclonal antibody samples.

3. The method of claim 1, wherein displaying the nodes and displaying the connections includes printing on paper.

4. The method of claim 1, wherein the interactions are pairwise interactions.

5. The method of claim 1, wherein nodes representing antibodies in the common bin are grouped together by proximity.

6. The method of claim 1, wherein nodes representing antibodies in a common bin are grouped together by matching one or more of shape, size, border, color, graphic, line thickness, or line type.

7. The method of claim 1, wherein nodes representing antibodies in a common bin are grouped together by displaying an envelope surrounding the nodes.

8. The method of claim 1, wherein connections between nodes in different bins are represented differently than connections between nodes in a common bin.

9. The method of claim 1, further comprising highlighting one or more of individual antibodies, individual connections, groups of antibodies, or groups of connections.

10. The method of claim 1, wherein the label-free biosensor is configured to simultaneously analyze a plurality of antibody interactions.

11. The method of claim 1, wherein all of the antibodies of a test panel are tested for all interactions of the test panel and the displaying the nodes displays the results of testing all interactions of the test panel.

12. The method of claim 1, wherein displaying connections includes displaying cross blocking interactions between nodes.

13. The method of claim 1, wherein displaying connections includes displaying one-directional interactions between the nodes.

14. The method of claim 1, wherein displaying connections includes simultaneous displaying interactions between one or more of the nodes in different locations on the graphical interface.

15. The method of claim 1, wherein displaying connections includes displaying a node graphically indicating a self-blocking interaction.

16. The method of claim 1, wherein displaying connections includes displaying a node graphically indicating inactive antibodies.

17. The method of claim 1, wherein displaying connections displays the connections to a user for a guided development of therapeutic antibodies.

18. The method of claim 1, wherein nodes representing antibodies in the common bin are grouped together if the nodes have a same blocking behavior with respect to both a ligand and an analyte.

19. The method of claim 1, wherein displaying the nodes and displaying the connections includes displaying on an electronic display.

20. The method of claim 19, where the electronic display or underlying computing software provides the ability of a user to modify one or more graphical feature of the nodes, the connections, or both.

21. The method of claim 1, wherein the blocking interactions include one-direction blocking interactions.

22. The method of claim 21, wherein the blocking interactions and one-direction blocking interactions are represented by connections each having a different appearance.

23. The method of claim 1, wherein displaying the nodes further comprises displaying additional information about individual antibodies by varying one or more of shape, size, border, color, graphic, line thickness, or line type.

24. The method of claim 23, wherein the additional information comprises one or more of identifying antibodies that are inactive when immobilized on a surface but active in a solution, identifying antibodies that are inactive in both directions, identifying orphan antibodies, identifying non-orphan antibodies, on-rate, off-rate, or affinity.

25. The method of claim 24, wherein a background color of the nodes is varied on a color gradient representing values of one or more of on-rate, off-rate, and affinity.

26. The method of claim 1, wherein displaying the nodes further comprises displaying additional information about individual antibodies by displaying the nodes on coordinate axes.

27. The method of claim 26, wherein the nodes are displayed on an isoaffinity plot with one coordinate axis representing on-rate and the other coordinate axis representing off-rate.

28. The method of claim 1, wherein displaying the connections further comprises displaying additional information about individual connections by varying one or more of connection line thickness, line type, or line color.

29. The method of claim 28, the additional information comprises one or more of number of replicates for the antibodies connected by the connection that were present in the assay, and heterogeneity in the blocking results.

30. The method of claim 1, wherein the antibodies are from is a first test panel further comprising displaying nodes and connections for antibodies from a second test panel, wherein a union of the nodes and connections of the first and second test panels is displayed.

31. The method of claim 30, further comprising displaying connections to identify untested interactions between pairs of antibodies that were not both present in either the first test panel or the second test panel.

32. The method of claim 1, wherein the label-free biosensor identifies interactions through surface plasmon resonance imaging.

33. The method of claim 32, wherein the label-free biosensor is operatively associated with a continuous flow microspotting unit.

34. The method of claim 1, wherein the label-free biosensor identifies interactions through biolayer interferometry.

35. The method of claim 34, wherein the label-free biosensor comprises a ligand coated fiber optic sensor.

36. A non-transitory computer readable storage medium containing instructions that can be read by at least one processor in connection with a-the label-free biosensor to cause the at least one processor and the label-free biosensor to perform the method of claim 1.

* * * * *